United States Patent
Carter et al.

[11] Patent Number: 5,919,201
[45] Date of Patent: Jul. 6, 1999

[54] SURGICAL SCALPEL

[75] Inventors: Michael J. Carter, Monmouth Junction; Simon Cohn, North Arlington; Jon D. Swenson, Wayne, all of N.J.; Noel Gharibian, Glendale, Calif.

[73] Assignee: Becton, Dickinson and Company, Franklin Lakes, N.J.

[21] Appl. No.: 09/052,147

[22] Filed: Mar. 31, 1998

Related U.S. Application Data

[63] Continuation-in-part of application No. 08/666,734, Jun. 18, 1996, abandoned, which is a continuation-in-part of application No. 08/376,065, Jan. 20, 1995, Pat. No. 5,527,329, which is a continuation of application No. 08/163,938, Dec. 8, 1993, abandoned.

[51] Int. Cl.$^6$ ................................................ A61B 17/32
[52] U.S. Cl. .................................. 606/167; 30/2; 30/151; 30/335
[58] Field of Search ..................................... 606/166, 167, 606/170; 30/2, 151, 158, 167, 335, 339

[56] References Cited

U.S. PATENT DOCUMENTS 5,662,669  9/1997  Abidin et al. ............................ 606/167

Primary Examiner—Michael Biuz
Assistant Examiner—William W. Lewis
Attorney, Agent, or Firm—Arthur D. Dawson

[57] ABSTRACT

A surgical scalpel includes a handle with a proximal end and a distal end that defines a cavity with an open distal end within the handle. The handle further includes an opening. The scalpel of the invention has a cartridge removably mountable to the handle. The cartridge includes a blade holder with a proximal end and a distal end. The blade holder includes elements for removably mounting the cartridge to the handle. There is a blade fixedly attached to the blade holder so that the blade projects distally. The scalpel of has a shield mounted on the blade holder for slidable movement between a distal position wherein the shield substantially prevents inadvertent access to the blade and a proximal position wherein the shield is substantially within the handle and the blade is exposed for use. The shield has a latch for engaging the blade holder and releasably retaining the shield in both the distal position and the proximal position.

19 Claims, 32 Drawing Sheets

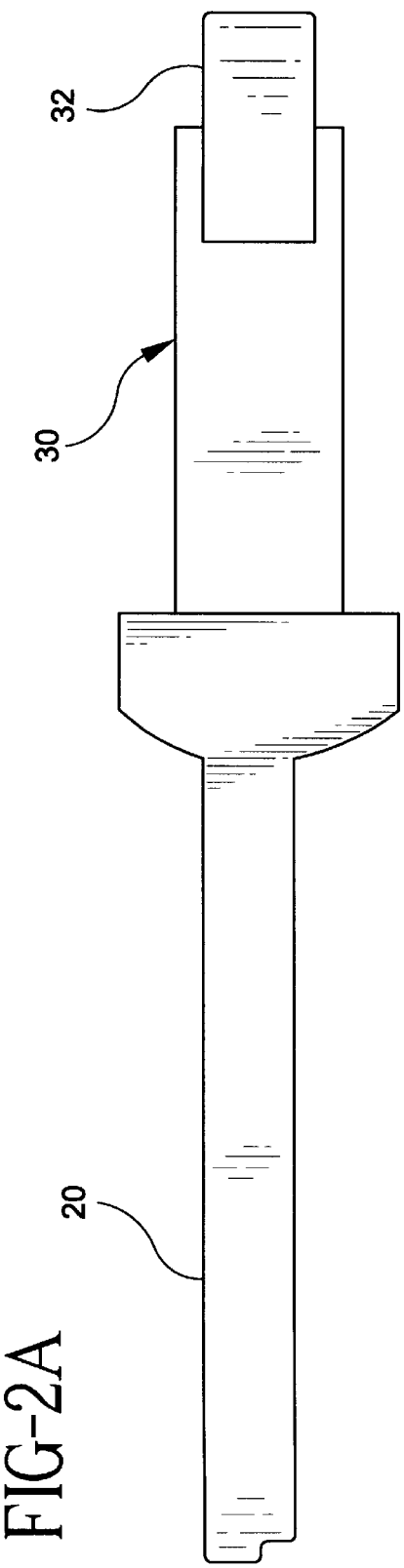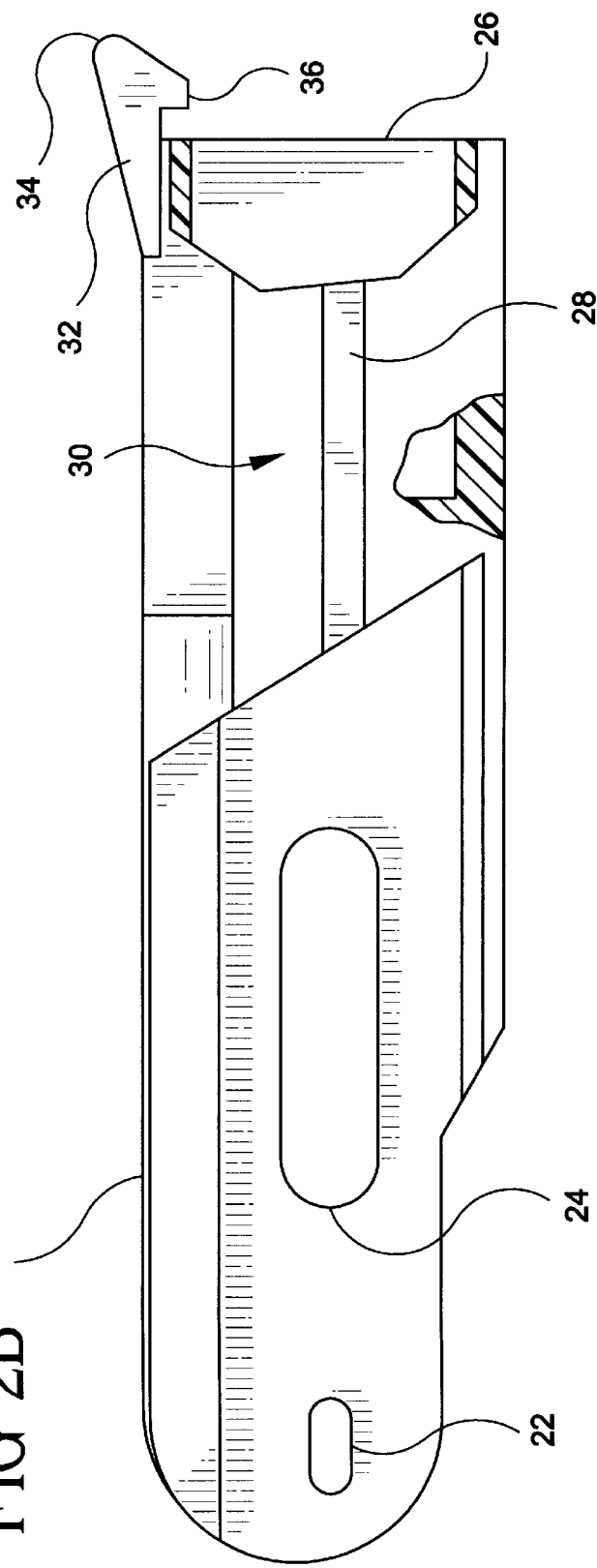

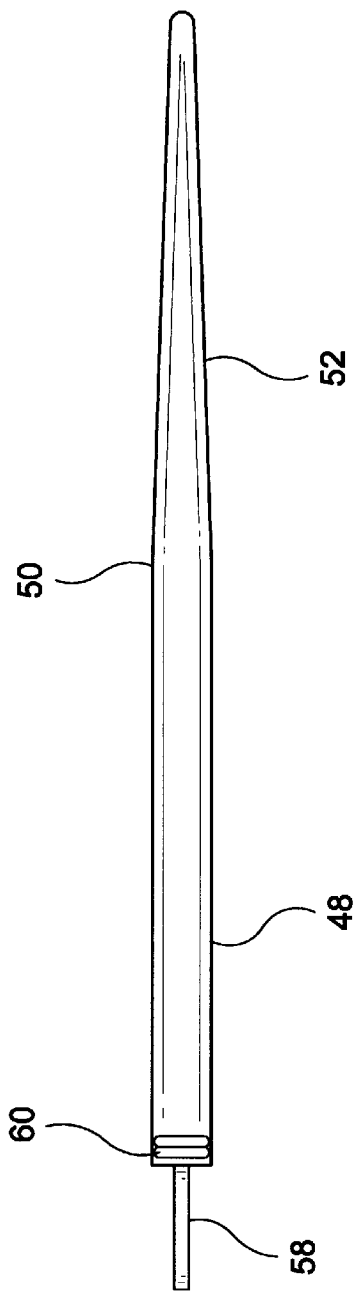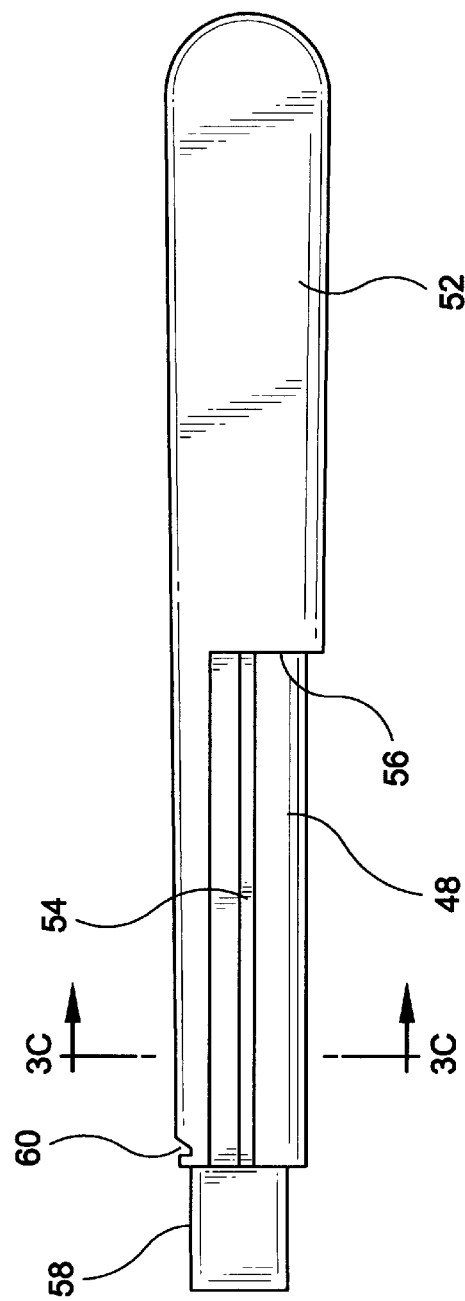

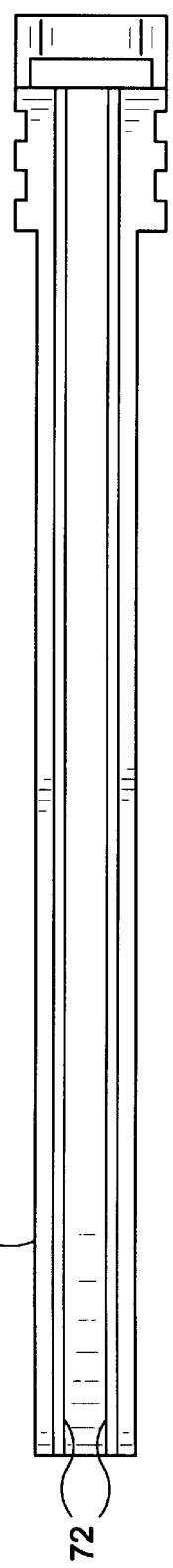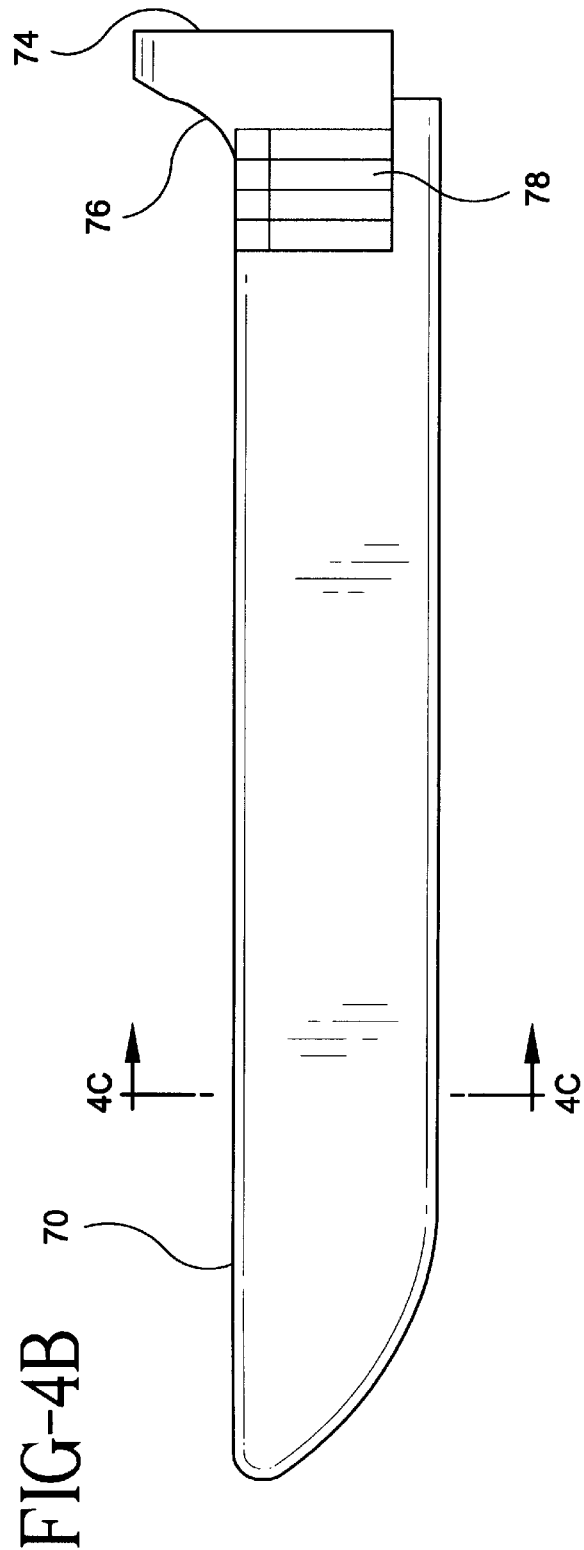

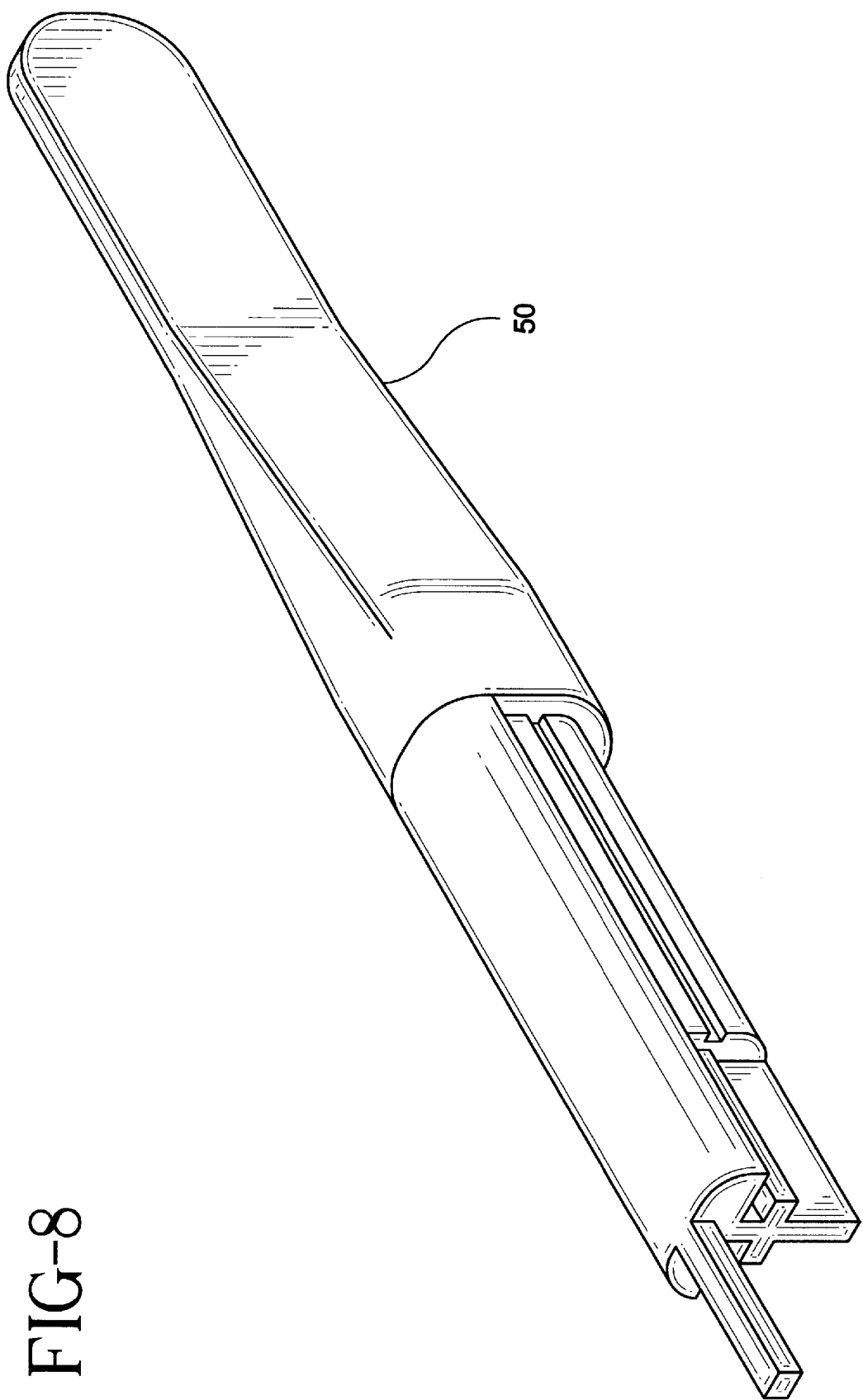

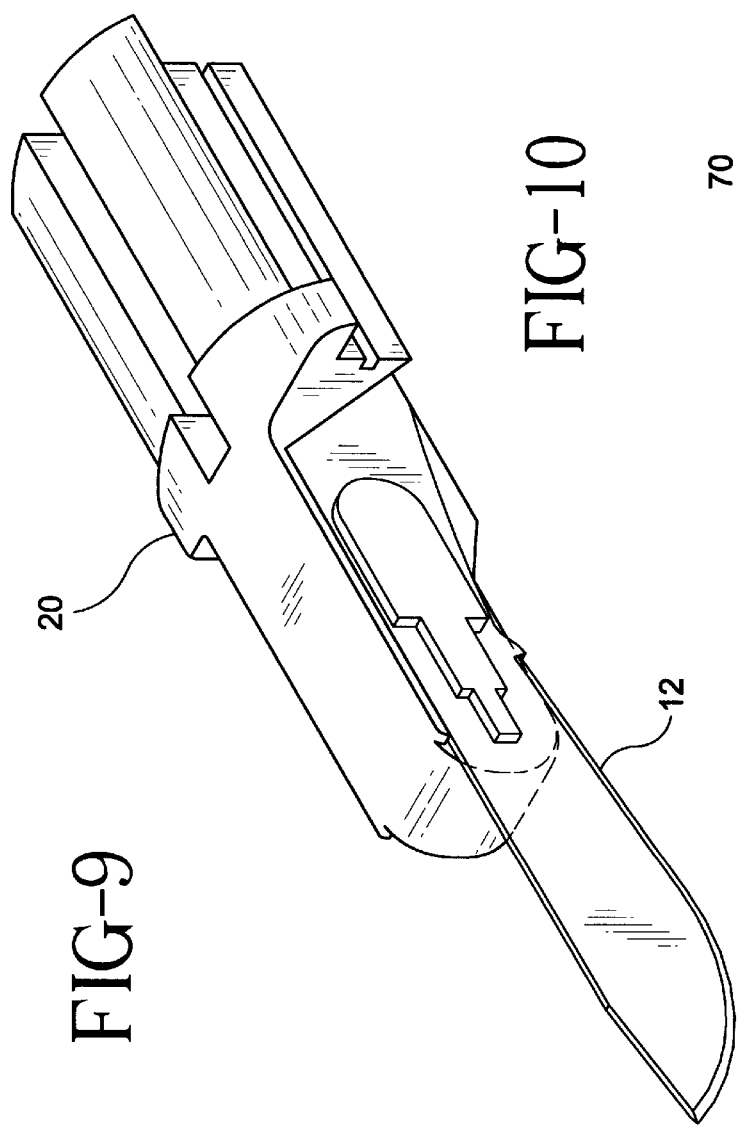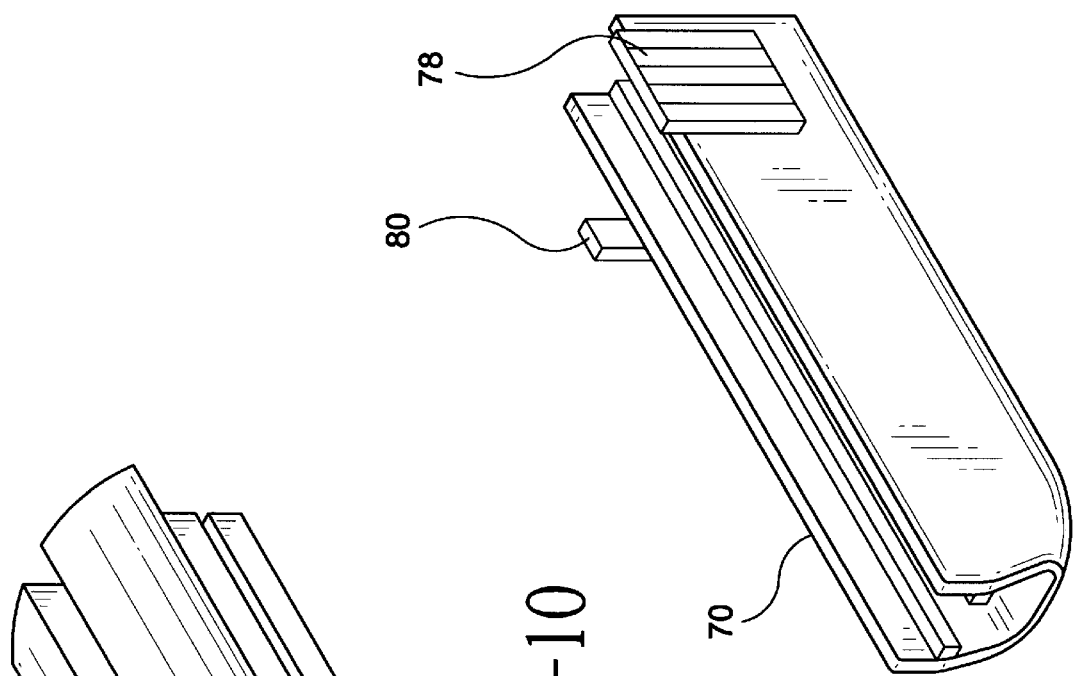

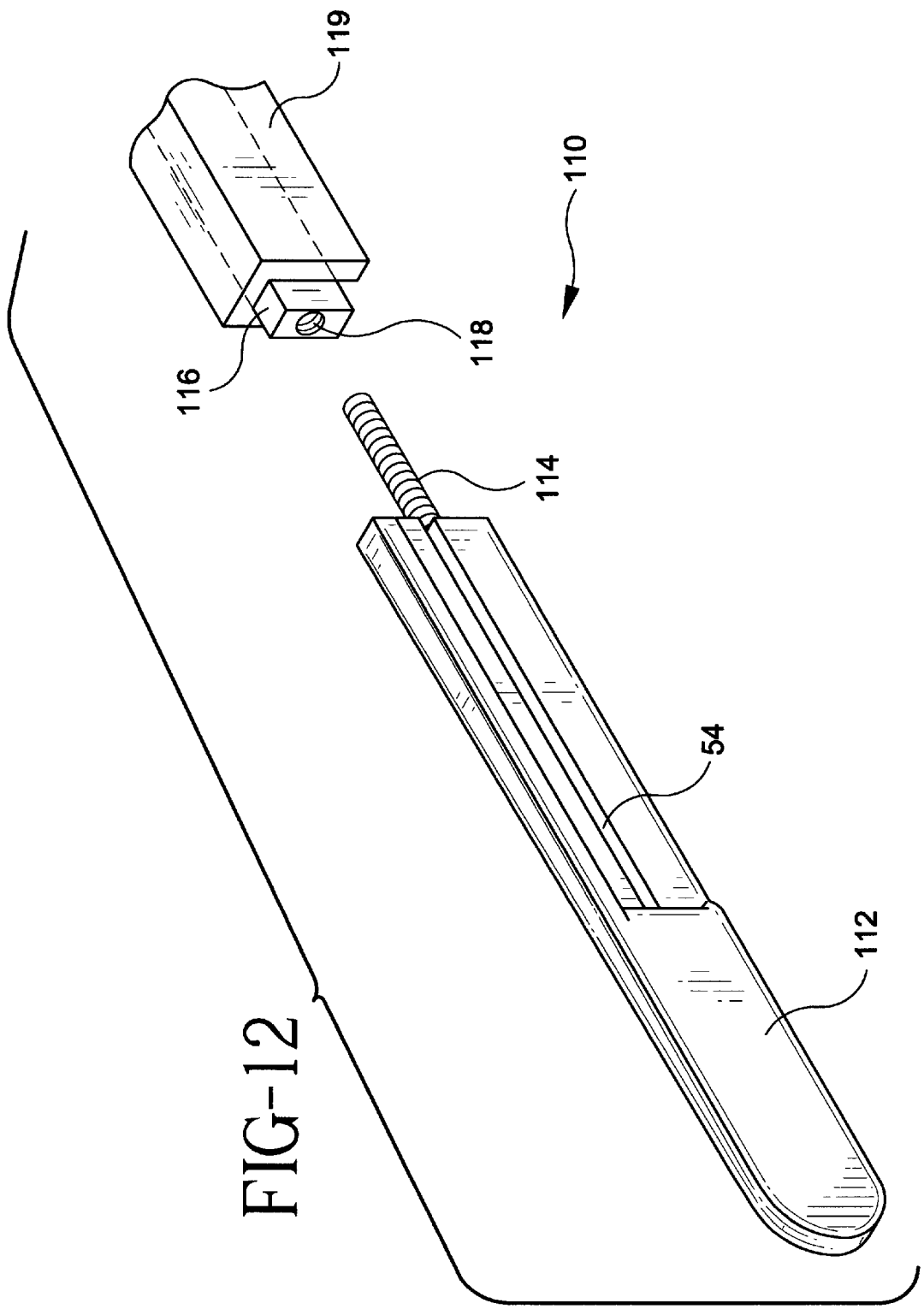

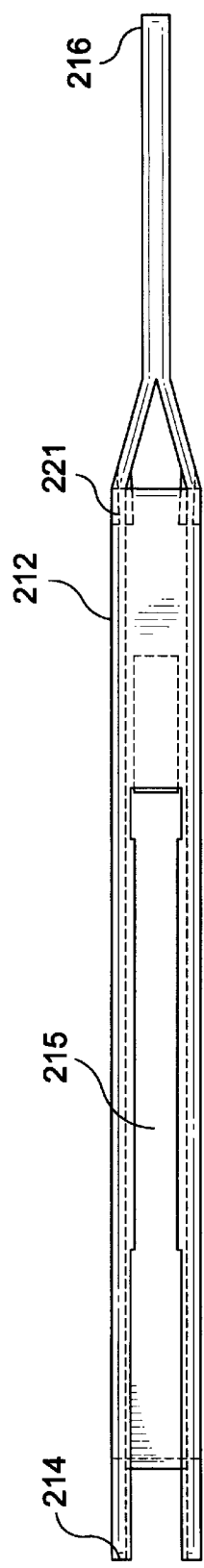
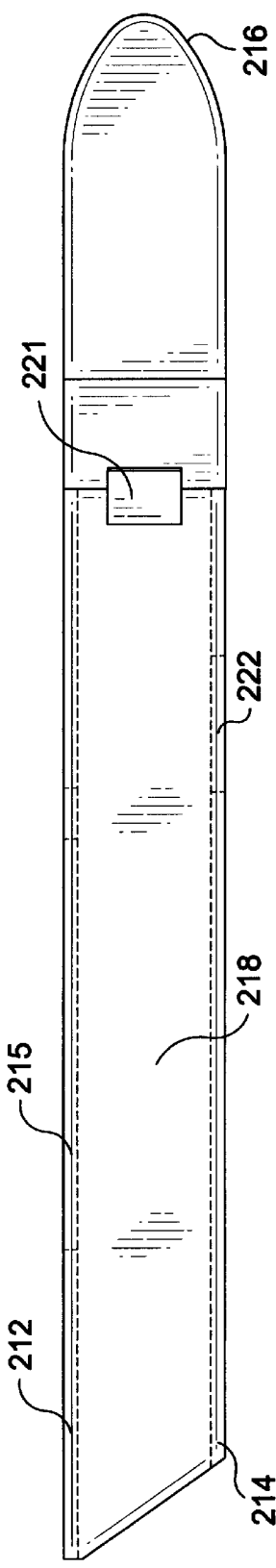
FIG-27
FIG-28

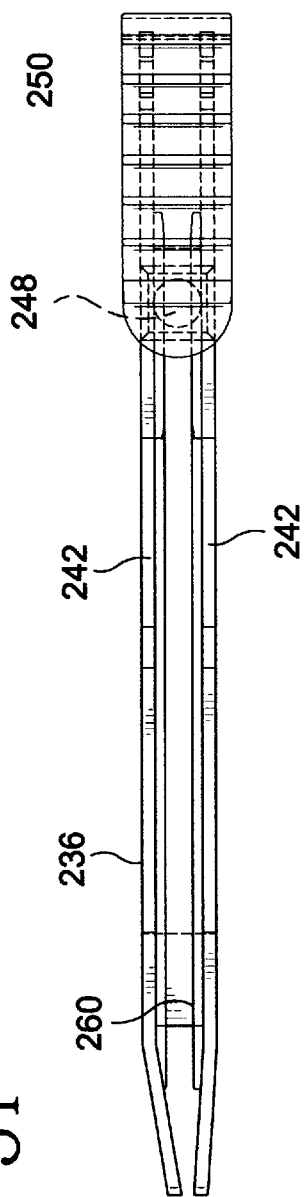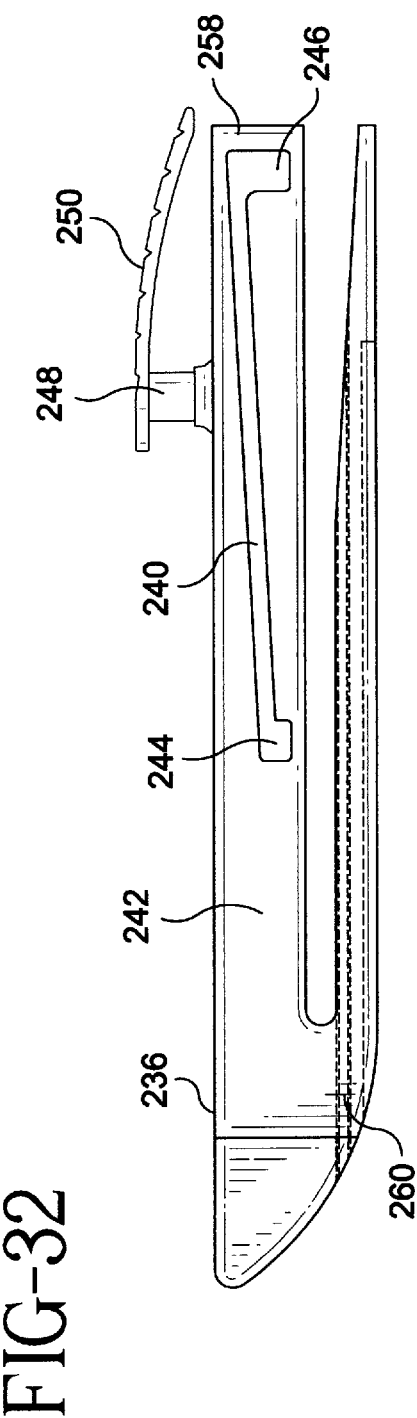

SURGICAL SCALPEL

This application is a Continuation-In-Part of patent application Ser. No. 08/666,734 filed Jun. 18, 1996, abandoned which is a Continuation-In-Part of patent application Ser. No. 08/376,065 filed Jan. 20, 1995 that is now U.S. Pat. No. 5,527,329, issued Jun. 18, 1996, which is a Continuation Application of patent application Ser. No. 08/163,938 filed on Dec. 8, 1993, abandoned.

The field of the invention is surgical cutting instruments. Conventional surgical instruments provide a significant potential for harm to surgeons, nurses and other support personnel. In the operating room, various surgical instruments are quickly passed by hand. The rapid handling of such instruments with exposed sharp edges can lead to accidental cuts or puncture wounds. Surgical gloves may also be inadvertently punctured leading to loss of glove integrity further increasing the risk of infection to a surgeon, nurse or other medical personnel.

Previous attempts to guard against inadvertent cuts or punctures led to the development of retractable blade guards. Some of the earliest versions were simply retractable bladed knives used in various industries outside the medical field. These blade guards generally required two hands to operate, i.e., one hand to manipulate the blade and a second hand to secure the blade guard by turning a threaded screw. Other conventional devices having spring loaded moving parts or tabs that clipped into notches on a hollow tubed sheathing device, were not practical for surgical use because they did not provide a good grip or "feel" for the blade.

SUMMARY

A surgical scalpel of the present invention includes a handle with a proximal end and a distal end that defines a cavity with an open distal end within the handle. The handle further includes an opening. The scalpel of the invention has a cartridge removably mountable to the handle. The cartridge includes a blade holder with a proximal end and a distal end. The blade holder includes elements for removably mounting the cartridge to the handle. There is a blade fixedly attached to the blade holder so that the blade projects distally when the cartridge is mounted to the handle. The scalpel of the invention has a shield mounted on the blade holder for slidable movement between a distal position wherein the shield substantially prevents inadvertent access to the blade and a proximal position wherein the shield is substantially within the handle and the blade is exposed for use. The shield has a latch for engaging the blade holder and releasably retaining the shield in both the distal position and the proximal position.

The scalpel of the invention provides practitioners with a scalpel that has the feel and weighting of a traditional reusable scalpel with the benefits of a fresh blade and a shield that substantially prevents inadvertent access to the sharp blade and that is intuitively movable from the distal position where the blade is protected to the proximal position to expose the blade. The replaceable cartridge allows the personnel charged with arming and disarming the scalpel to handle only a protected blade and substantially prevents operating room personnel from being exposed to the blade during set-ups and transfers of equipment during procedures.

BRIEF DESCRIPTION OF THE DRAWINGS

In the drawings, wherein similar reference numbers denote similar elements throughout the several views:

FIG. 2a is a top view of the blade holder;

FIG. 2b is a side elevation view of the blade holder illustrating the position of the hook in the preferred embodiment and illustrating a partial section view of the attachment slot;

FIG. 3a is a top view of the handle shown in FIG. 1;

FIG. 3b is a side elevation view of the handle illustrating the groove and a male end attachment flange;

FIG. 4a is a top view of the sleeve;

FIG. 4b is a side elevation view thereof;

FIG. 8 is a perspective view of a second alternative embodiment of the handle;

FIG. 9 is a perspective view of an alternative embodiment of the blade holder having a female end connection;

FIG. 10 is a perspective view of an alternative embodiment of the sleeve;

FIG. 12 is an exploded partial perspective view of an alternative embodiment with the blade holder threaded onto the handle;

FIG. 27 is a schematic top plan view of the handle portion of the scalpel of FIG. 16;

FIG. 28 is a schematic side elevation of the handle portion of the scalpel of FIG. 16;

FIG. 31 is schematic top plan view of the shield of the scalpel of FIG. 16; and

FIG. 32 is a schematic side elevation view of the shield of the scalpel of FIG. 16.

DETAILED DESCRIPTION

Figure 1:
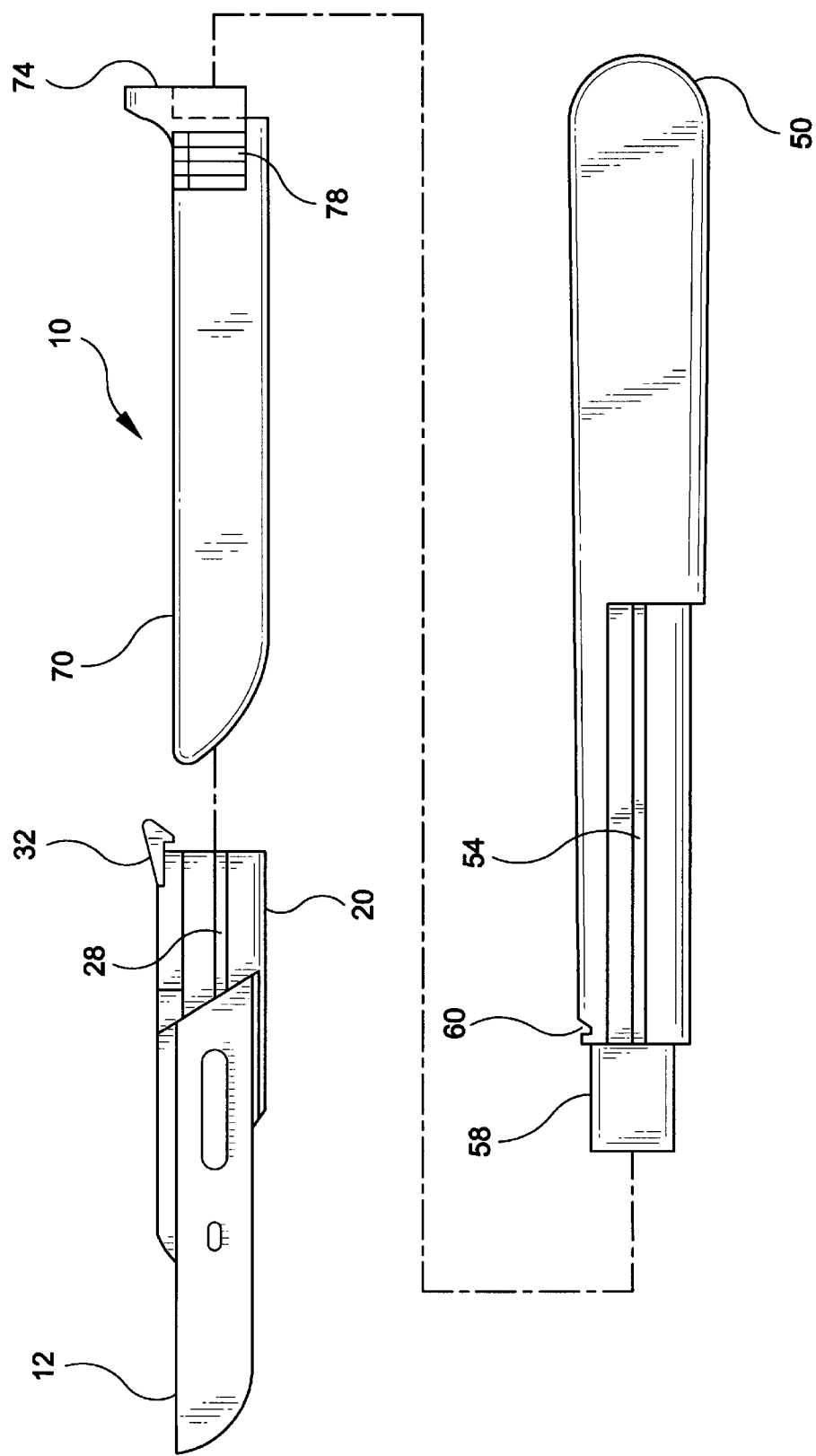
FIG. 1 is an exploded side elevation view of a preferred embodiment of the present scalpel.
Figure 2D:
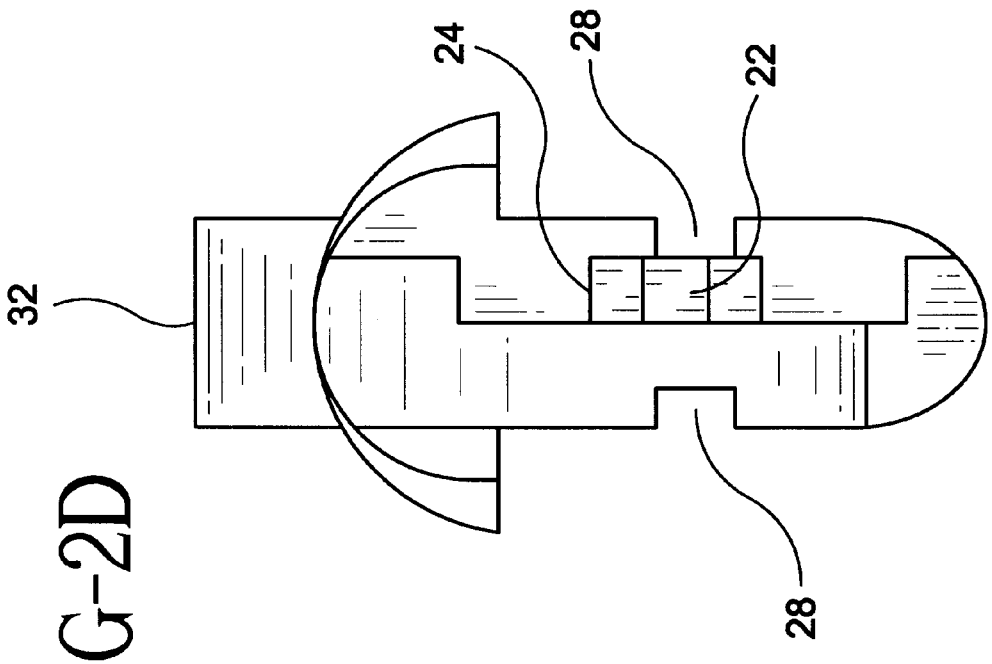
FIG. 2d is a front end view thereof.
Figure 2C:
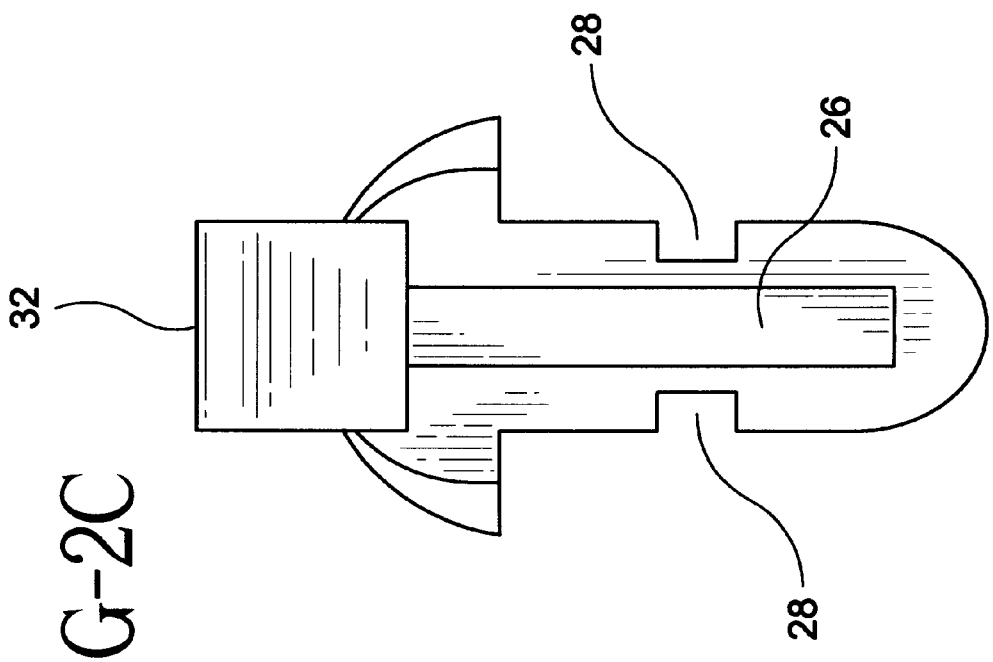
FIG. 2c is a back end view of the blade holder showing the hook and the attachment slot.

Turning in detail to the figures, the surgical scalpel 10 is first shown in FIG. 1 with the blade 12 secured to the blade holder 20. The scalpel 10 is gripped by the handle 50 which has a preferably contoured elongated grip portion 52. As is shown in FIGS. 2a and 2b, adjacent the front end of the blade holder 20 are two tabs 22 and 24 for securing the blade 12 to the blade holder 20 by interlocking with respective openings on the blade 12. Adjacent the back end of the blade holder 20 is the attachment slot 26 shown as a female end connection. Channels 28 are positioned longitudinally on opposite sides of the blade holder 20 along a channel section 30 of the blade holder 20.

A hook 32 is cantilevered from the back end of the blade holder 20. The hook 32 can resiliently flex upwardly and downwardly to engage the handle 50. The cantilevered end of the hook 32 has an inclined aft surface 34 and a protrusion 36 which is adapted to engage a complementary shaped groove 60 on the handle 50 when the blade holder 20 mates with the handle 50.

Referring now to FIGS. 3a and 3b, a pair of guide channels 54 are provided on opposite sides of the guide channel section 48 of the handle 50 in front of the grip portion 52. The guide channels 54 terminate at detents where the guide channel section 48 adjoins the grip portion 52.

Figure 3D:
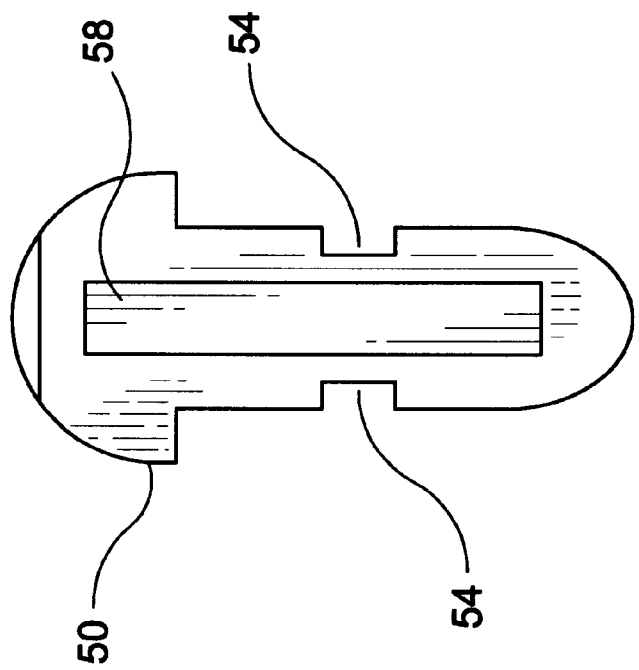
FIG. 3d is a front end view of the handle.
Figure 3C:
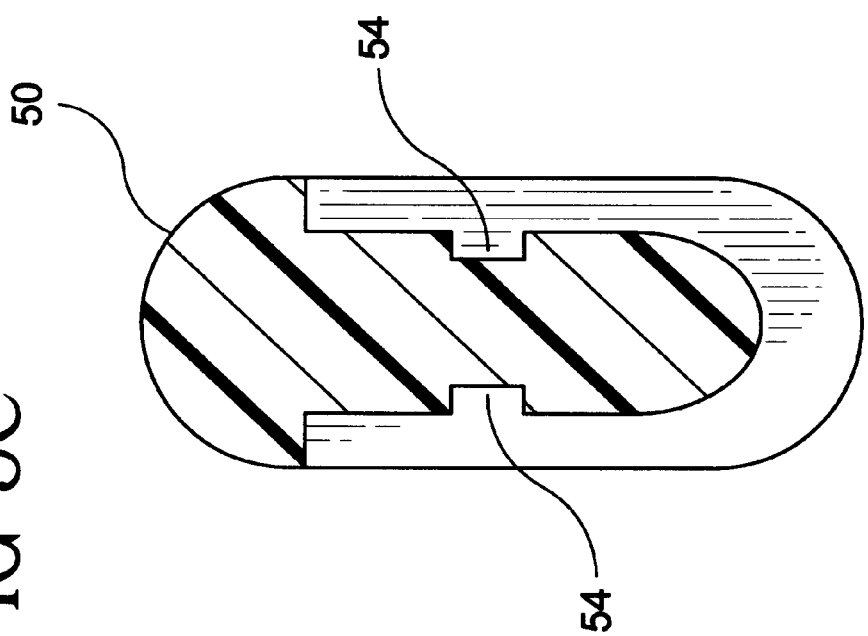
FIG. 3c is a section view taken along line 3c—3c of FIG. 3b.
Figure 4D:
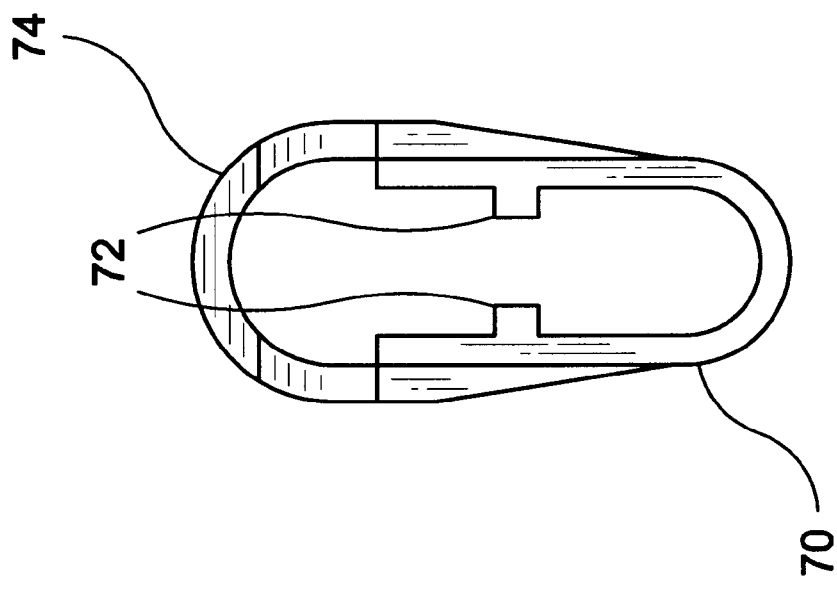
FIG. 4d is a front end view of the sleeve showing the arch.
Figure 4C:
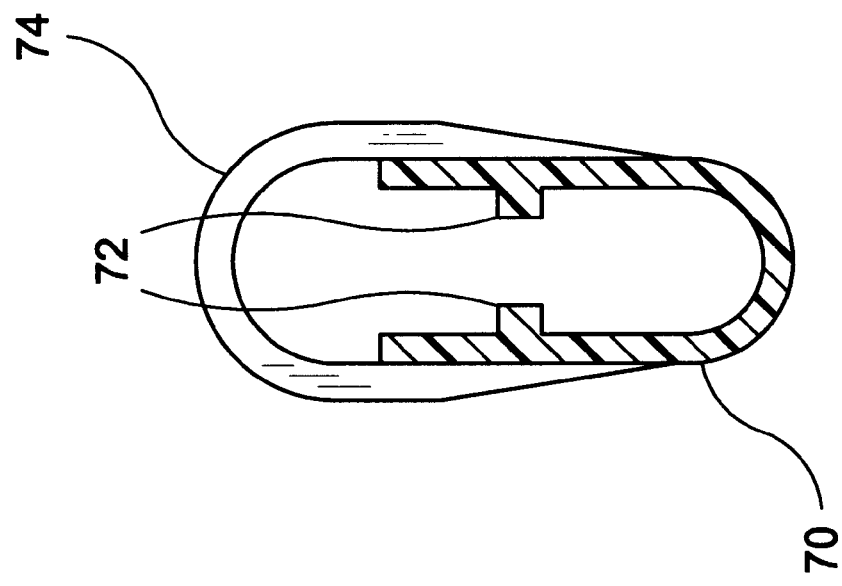
FIG. 4c is a section view of the sleeve taken along line 4c—4c of FIG. 4b.

An attachment flange 58 (shown as a male ended attachment) is joined to the front end of the guide channel section 48. As shown in FIGS. 3c and 3d, the attachment flange 58 is generally rectangular in cross section, although other configurations are possible, and is adapted to mate with the attachment slot 26 of the blade holder 20. A groove 60 at the forward end of the guide channel section 48 is shaped to mate with the hook 32.

Next referring to FIGS. 4a through 4d, the sleeve 70 is generally U-shaped in cross section having a closed bottom portion and an open upper portion. A pair of guide flanges 72 are positioned within the sleeve 70 spans between the two sides of the sleeve 70. The arch 74 preferably has a radiused front surface 76.

Figure 5A:
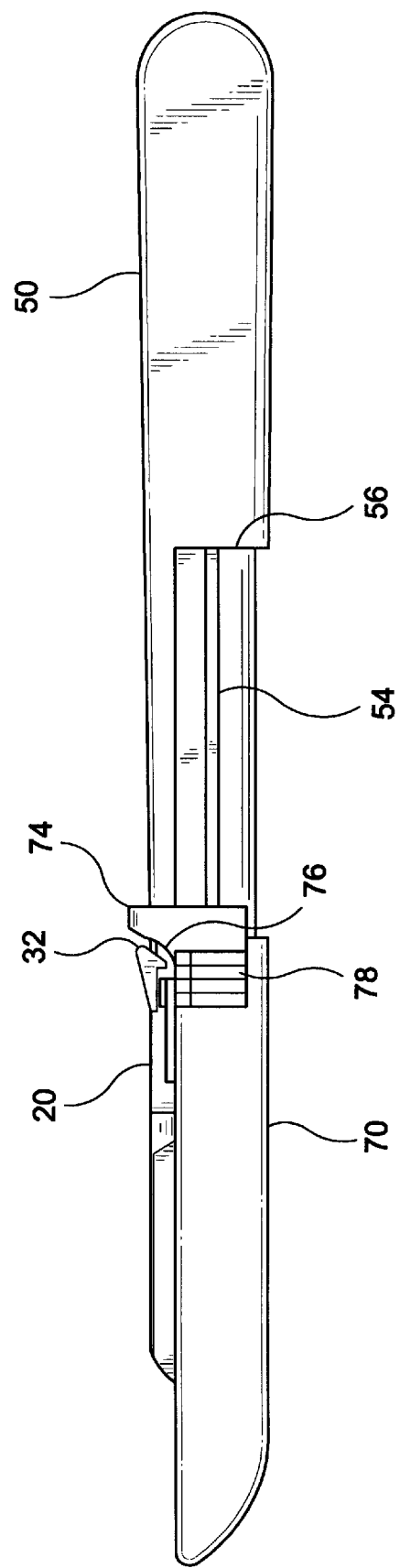
FIG. 5a is a side elevation view of the assembled scalpel with the sleeve positioned in an extended position.

The sleeve 70 preferably has a digit engaging portion 78 adjacent to the arch 74 having a series of ribs forming a thumb rest. The digit engaging portion 78 improves the surgeon's "feel" for the sleeve 70 when the sleeve 70 slides along the guide channels 28 and 54 by hand or thumb pressure. FIG. 5a shows an assembled scalpel 10 with the sleeve 70 in a forward position to cover the sheath of blade 12. The forward movement of the sleeve 70 is guided by the guide flanges 72 that travel along the guide channels 28 and 54. With the sleeve 70 moved fully forward, the radiused surface 76 contacts the hook 32 to stop additional forward movement.

Additional forward movement by the sleeve 70 toward the extended position as guided by the user's hand will cause the arch 74 to lift the hook 32 out of the groove 60 for removal of the blade holder 20 from the handle 50. This allows the sleeve 70 and blade holder 20 to be disassembled as a unit from the handle 50 while the blade 12 is sheathed by the sleeve 70, thus minimizing the risks of inadvertent cuts. The blade 12, blade holder and sleeve 70 may then be disposed of. The handle may advantageously be reused.

Figure 5B:
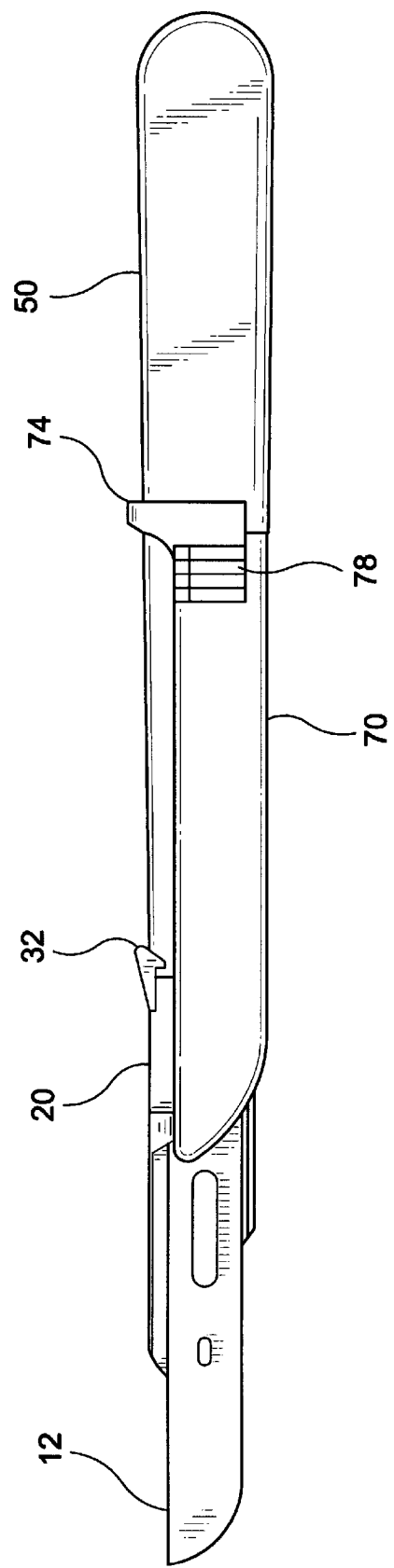
FIG. 5b is an elevation view thereof with the sleeve in a retracted position.
Figure 5C:
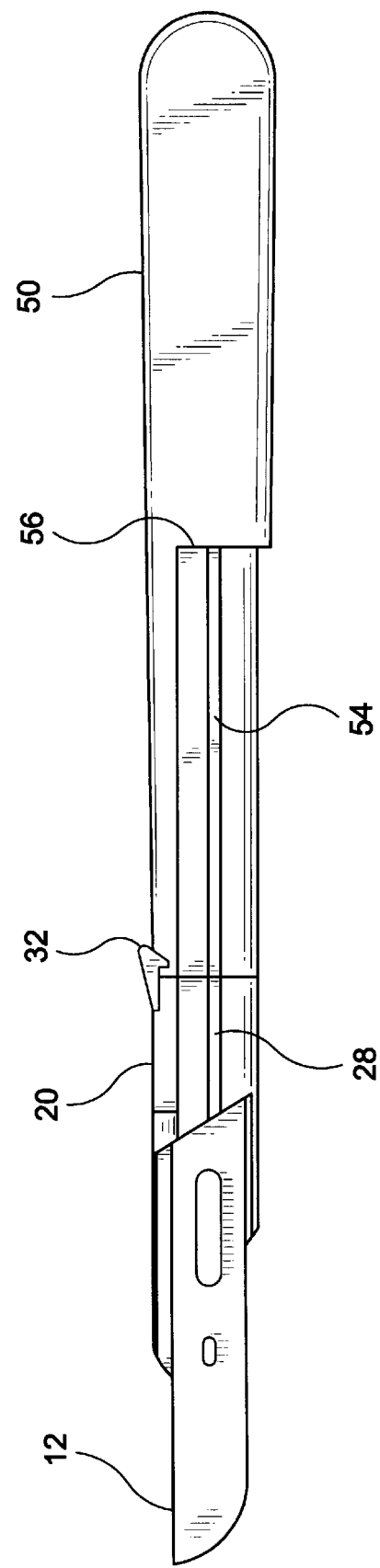
FIG. 5c is a side elevation view with the sleeve removed.

Figure 5b shows the sleeve 70 moved to the fully retracted position with the back end of the sleeve 70 abutting the detents 56 to fully expose the blade 12. The user may utilize the digit engaging portion 78 on the sleeve 70 to improve fingertip control of the longitudinal front to back movement of the sleeve 70. FIG. 5c shows the sleeve 70 removed from the handle 50 (for purposes of illustration).

Figure 6:
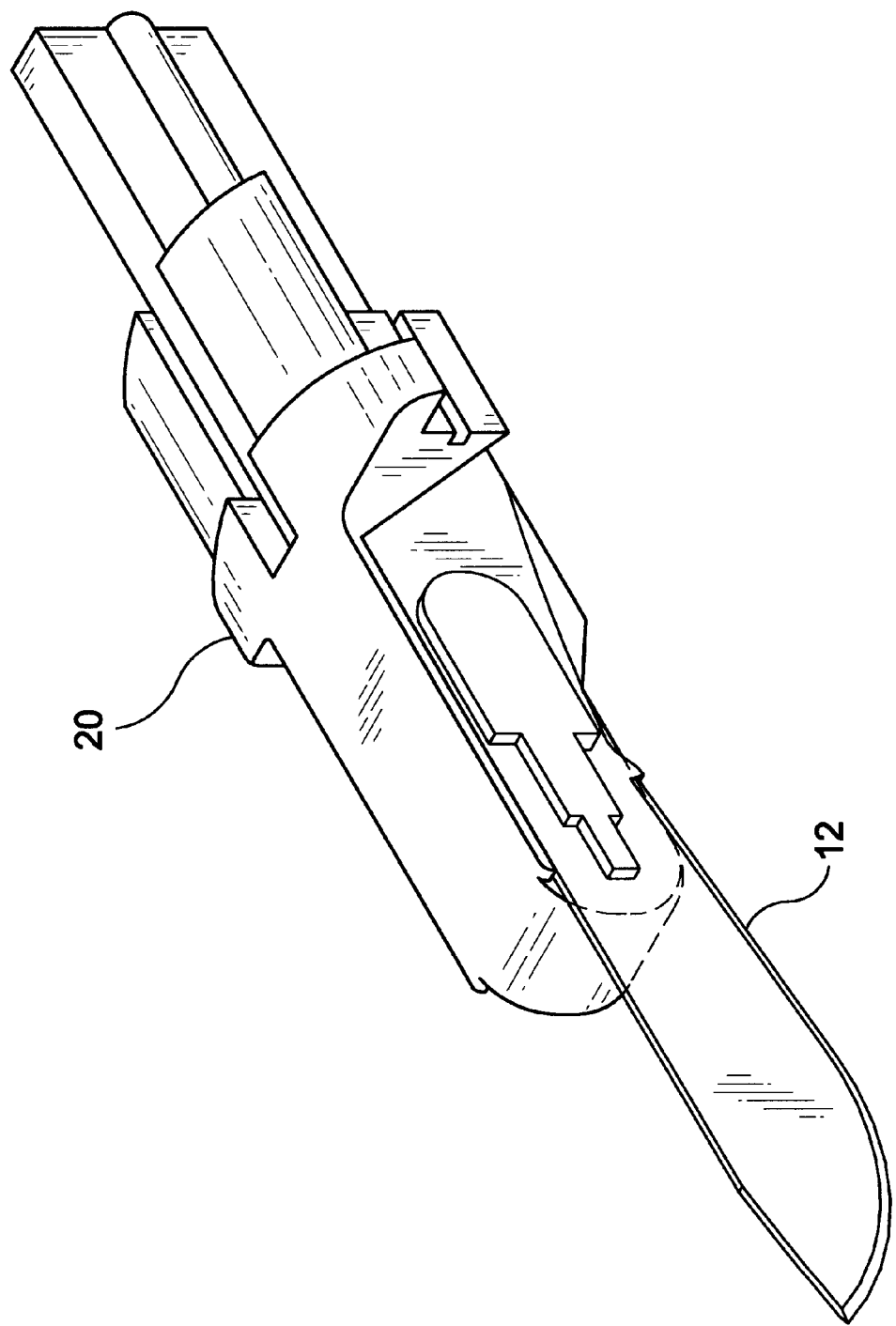
FIG. 6 shows a perspective of an alternative embodiment of the blade holder with the blade attached.
Figure 7:
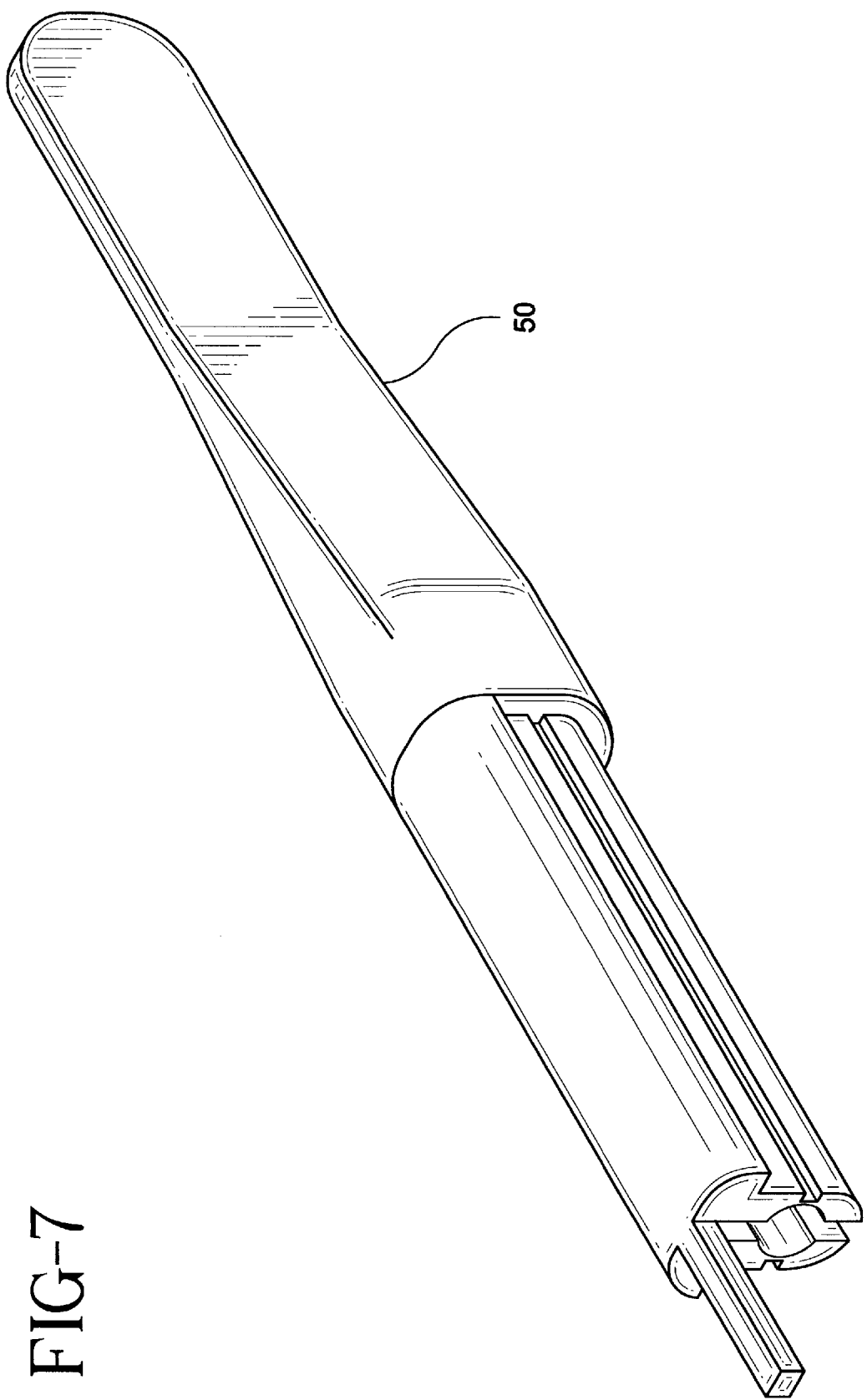
FIG. 7 is a perspective view of an alternative embodiment of the handle.

FIG. 6 illustrates an embodiment of the blade holder 20 with both a male ended attachment and a female ended slot. FIG. 7 shows an embodiment of the handle 50 which mates with the blade holder 20 shown in FIG. 6. An alternative embodiment of the handle 50 is also shown in FIG. 8 with male ended connections. An embodiment of the blade holder 20 which mates with the handle 50 of FIG. 8 is further shown in FIG. 9 with an outline of the attached blade 12. An alternative embodiment of the sleeve 70 is shown in FIG. 10 which illustrates a stop tab 80 which may be utilized to stop forward longitudinal sliding of the sleeve 70. An inclined digit engaging portion 78 is illustrated and may be used to facilitate use as a thumb rest for the operation surgeon.

Figure 11:
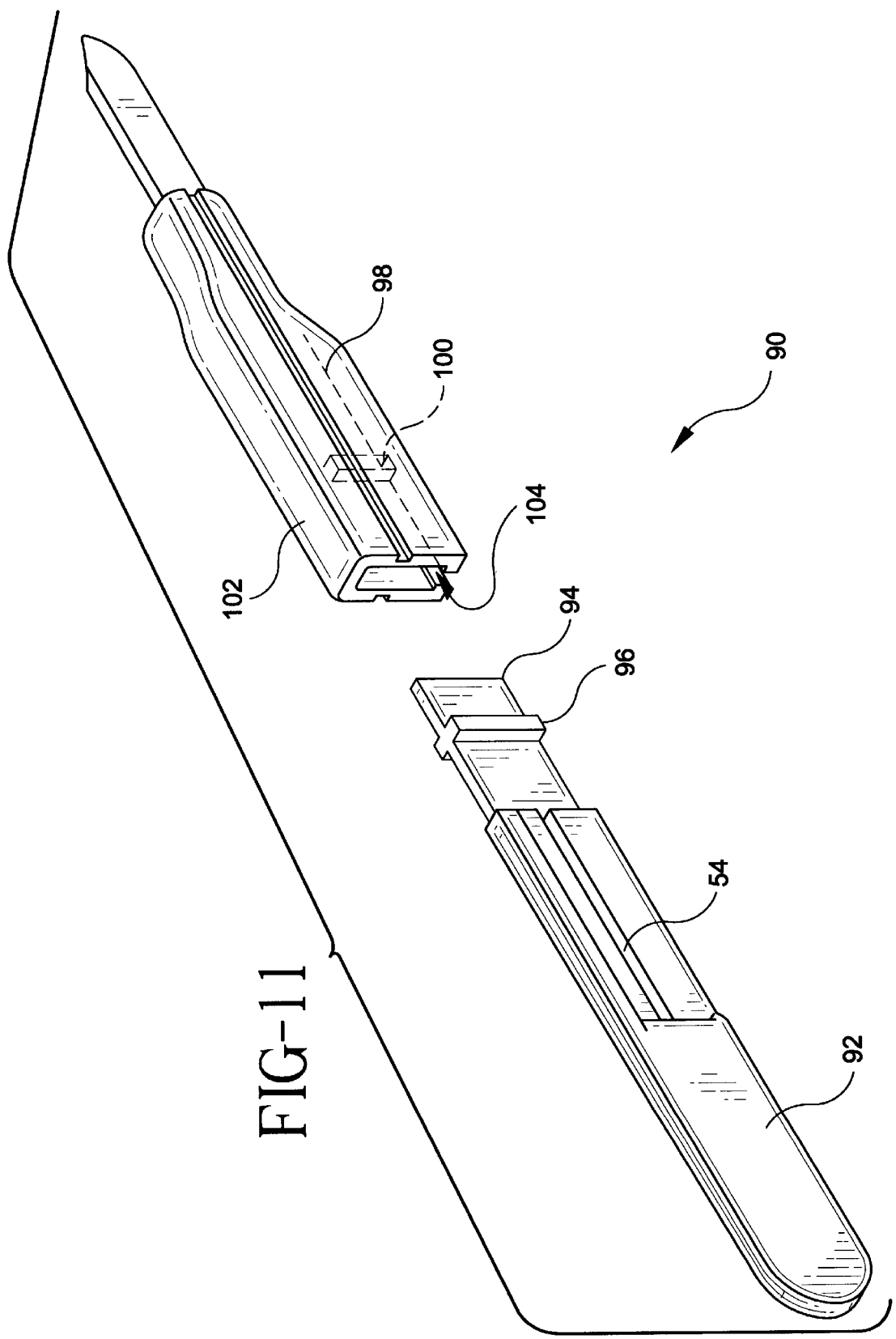
FIG. 11 is a perspective view of an alternative embodiment with the blade holder attached to the handle using vertical slots and tabs.

In an alternative embodiment 90 as shown in FIG. 11, a handle 92 has a flange 94 with vertical tabs or protrusions 96. A blade holder 98 has internal vertical slots 100 adapted to vertically slide down over the tabs 96 from above. A sleeve 102 is secured to the blade holder 98, as described above with reference to FIGS. 1–5. The sleeve 102 has a slot 104 at the back end of its lower surface. In use, the blade holder 98 is attached to the handle 92 by engaging the vertical tabs 96 into the vertical slots 100, by sliding the blade holder 98 down onto the handle 92 from above. The slot 104 in the bottom of the sleeve 102 provides sufficient clearance for the protruding vertical tabs 96.

Turning to FIG. 12, a surgical scalpel 110 has a handle 112 with a threaded stud 114 at its front end. The stud 114 threads into a threaded hole 118 at the back end of a blade holder 116. The threads on the stud 114 and in the threaded hole 118 are advantageously cut so that when the blade holder 116 bottoms out of the front end of the handle 112, the blade holder 116 will be properly vertically aligned. A sleeve 119 overlies the blade holder 116. The operation and design features of the surgical scalpels shown in FIGS. 11 and 12 are similar to the embodiment in FIGS. 1–5, except as described above.

Figure 14:
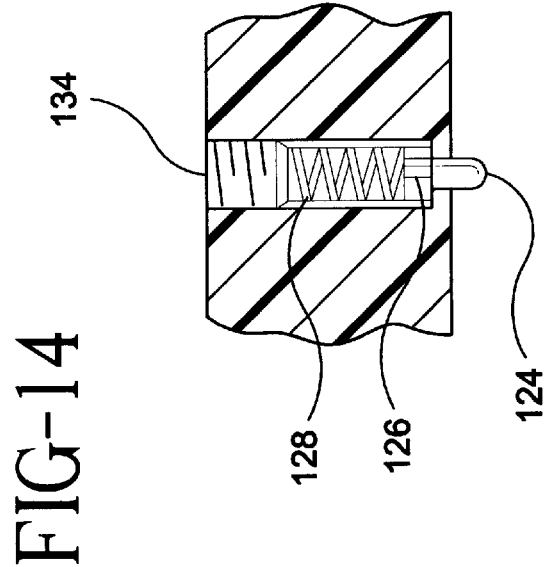
FIG. 14 is an enlarged section view of the locking button of FIG. 13.
Figure 13:
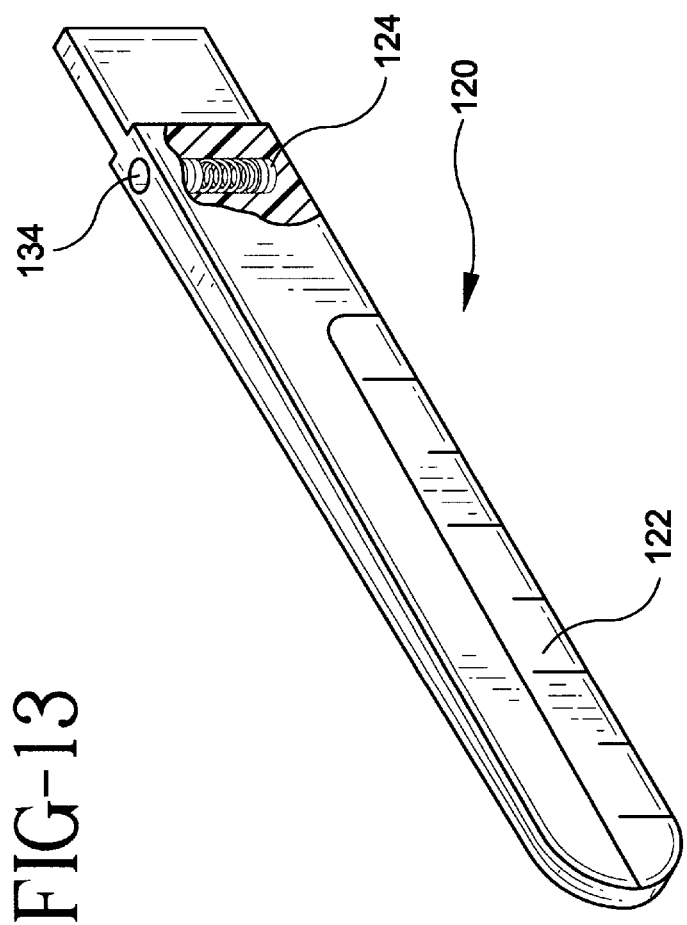
FIG. 13 is a perspective view in part section of an alternative handle embodiment having a button for locking the shield in position over the blade.
Figure 15:
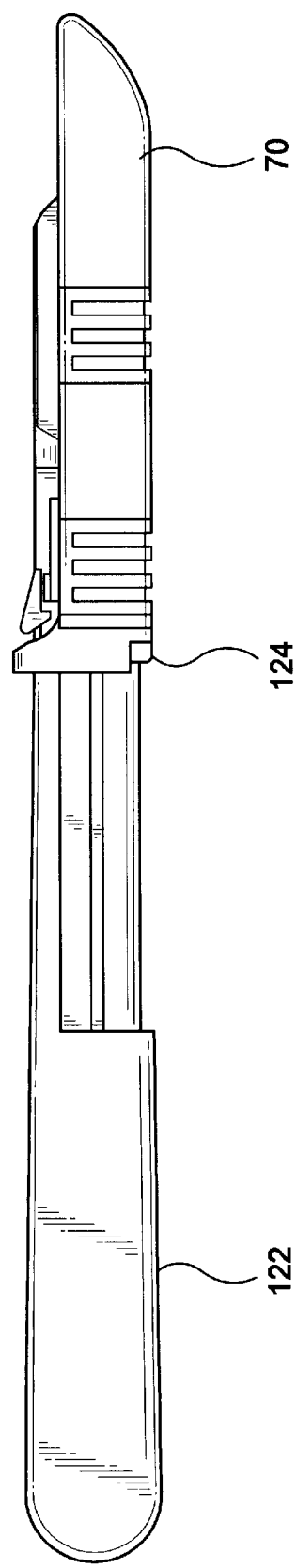
FIG. 15 is a side elevation view of the button of FIG. 14 locking the shield in its extended position.

As shown in FIG. 13 an alternative handle embodiment 122 has a locking button 124. As shown in FIG. 14, the locking button 124 has a shoulder 126 which fits within a bore 130 in the handle 122. A plug or set screw 134 at the top of the handle 122 retains a spring 128 in the bore 130, with the spring 128 biasing the locking button 124 to protrude out of the bottom surface of the handle 122. Referring to FIG. 15, with the shield 70 fully extended to cover the blade, 12, the locking button 124 protrudes out of the bottom of the handle 122. The sleeve 70 can not be retracted to expose the blade, without first pushing the locking button 124 up into the bore 130. Once the locking button 124 is pushed up into the bore 130, the sleeve 70 may be retracted, with the locking button sliding in the inside lower wall or surface of the sleeve. Accordingly, the locking button 124 helps to prevent inadvertent exposing of the blade 12. The locking button feature may be used on any of the surgical scalpel embodiments described above.

While a preferred embodiment of the present invention has been shown and disclosed in the drawings and specifications, alternate embodiments of the present invention would be apparent to the person of ordinary skill in the art and this application is intended to include those embodiments within the full breadth and scope of the claims. Moreover, the present invention need not include all of the features disclosed in the single embodiment but rather one or more features may be included.

While this invention is satisfied by embodiments in many different forms, there are shown in the drawings and herein described in detail, embodiments of the invention with the understanding that the present disclosure is to be considered as exemplary of the principles of the present invention and is not intended to limit the scope of the invention to the embodiments illustrated. The scope of the invention is measured by the appended claims and their equivalents. In this disclosure, the term "proximal" refers to the portions of the device closest to the practitioner and the term "distal" refers to the portion of the device away from the practitioner.

Figure 18:
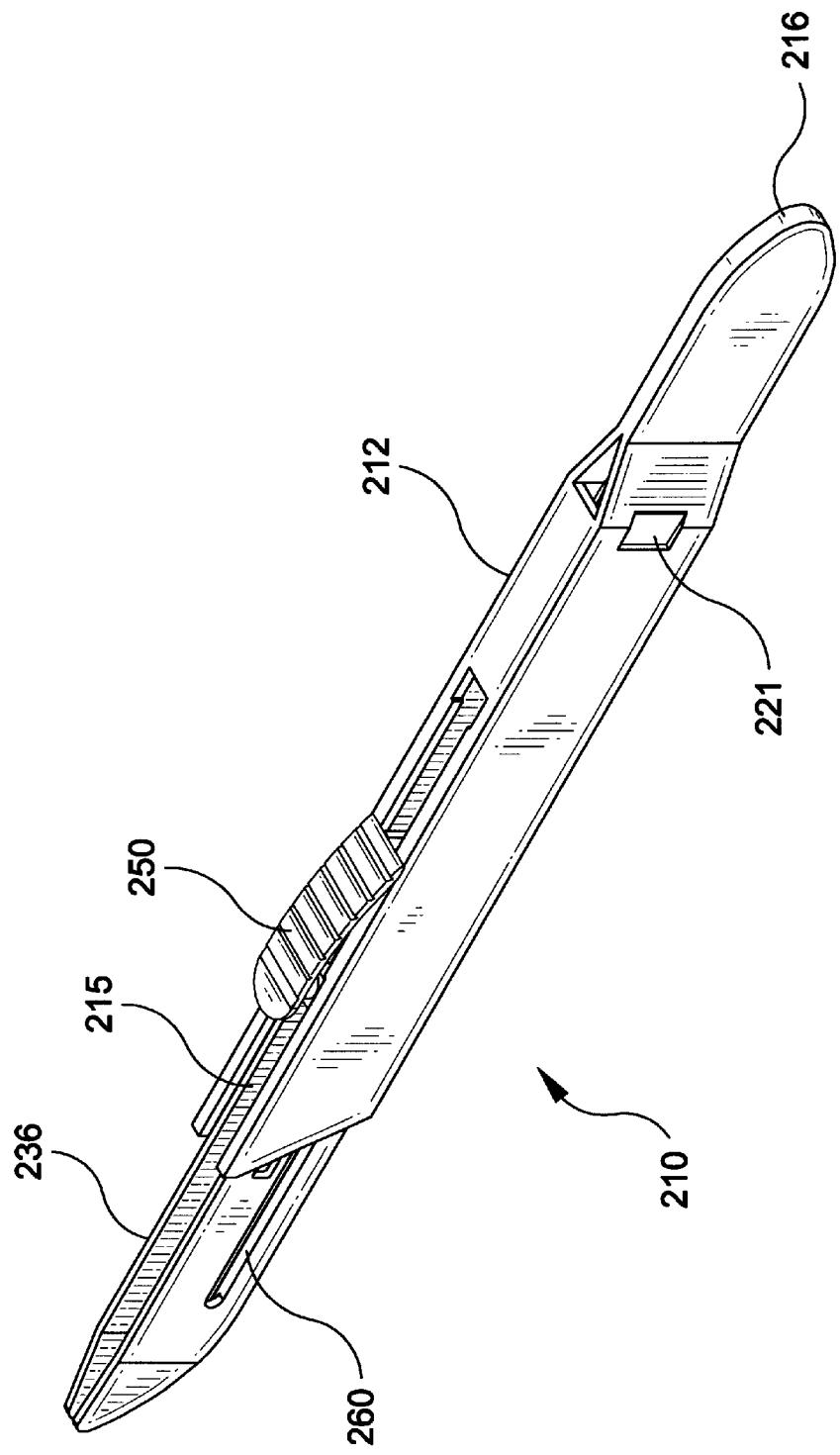
FIG. 18 is a perspective view of the surgical scalpel of FIG. 16 as assembled.
Figure 19:
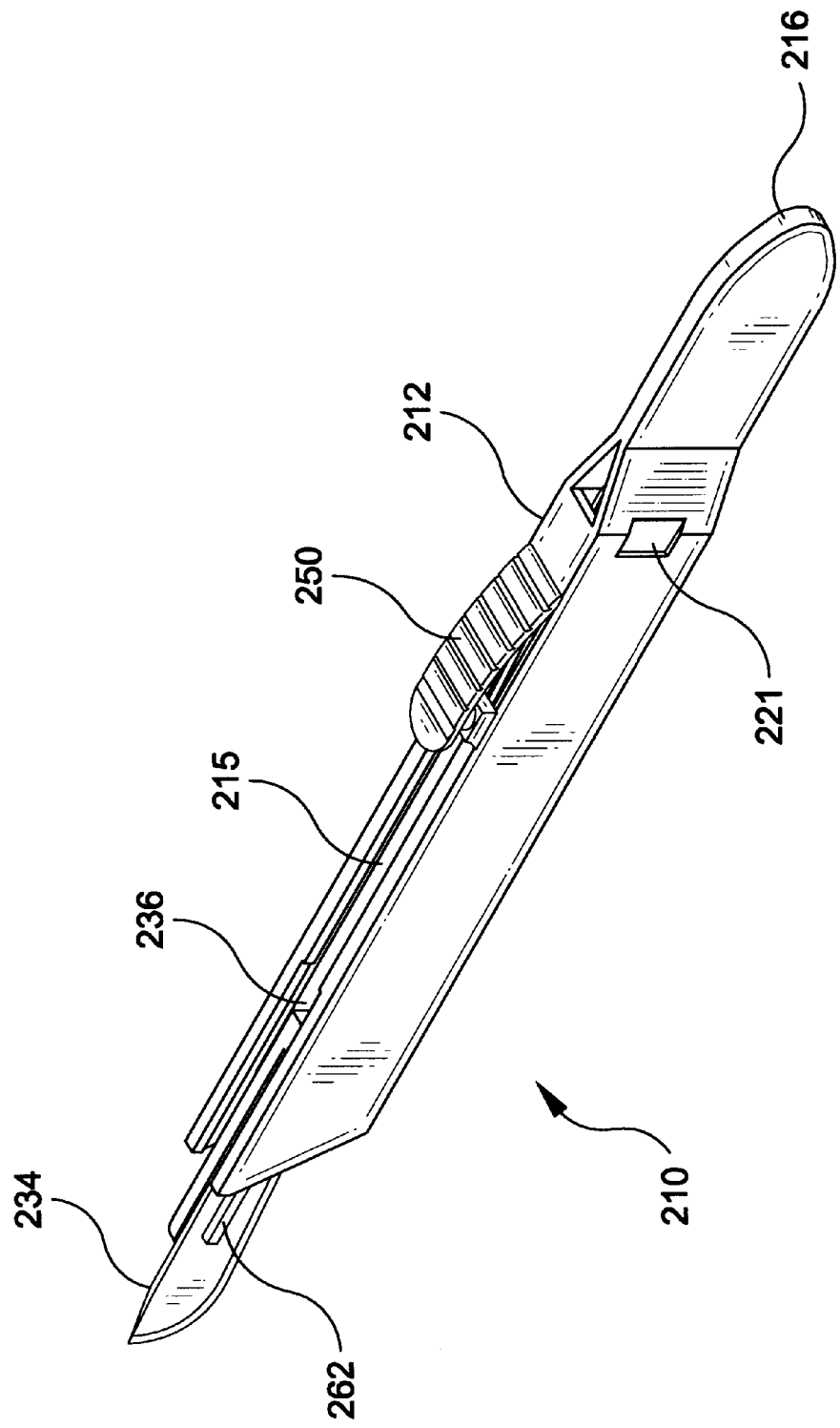
FIG. 19 is a perspective view of the surgical scalpel of FIG. 16 with the shield in the proximal position.
Figure 20:
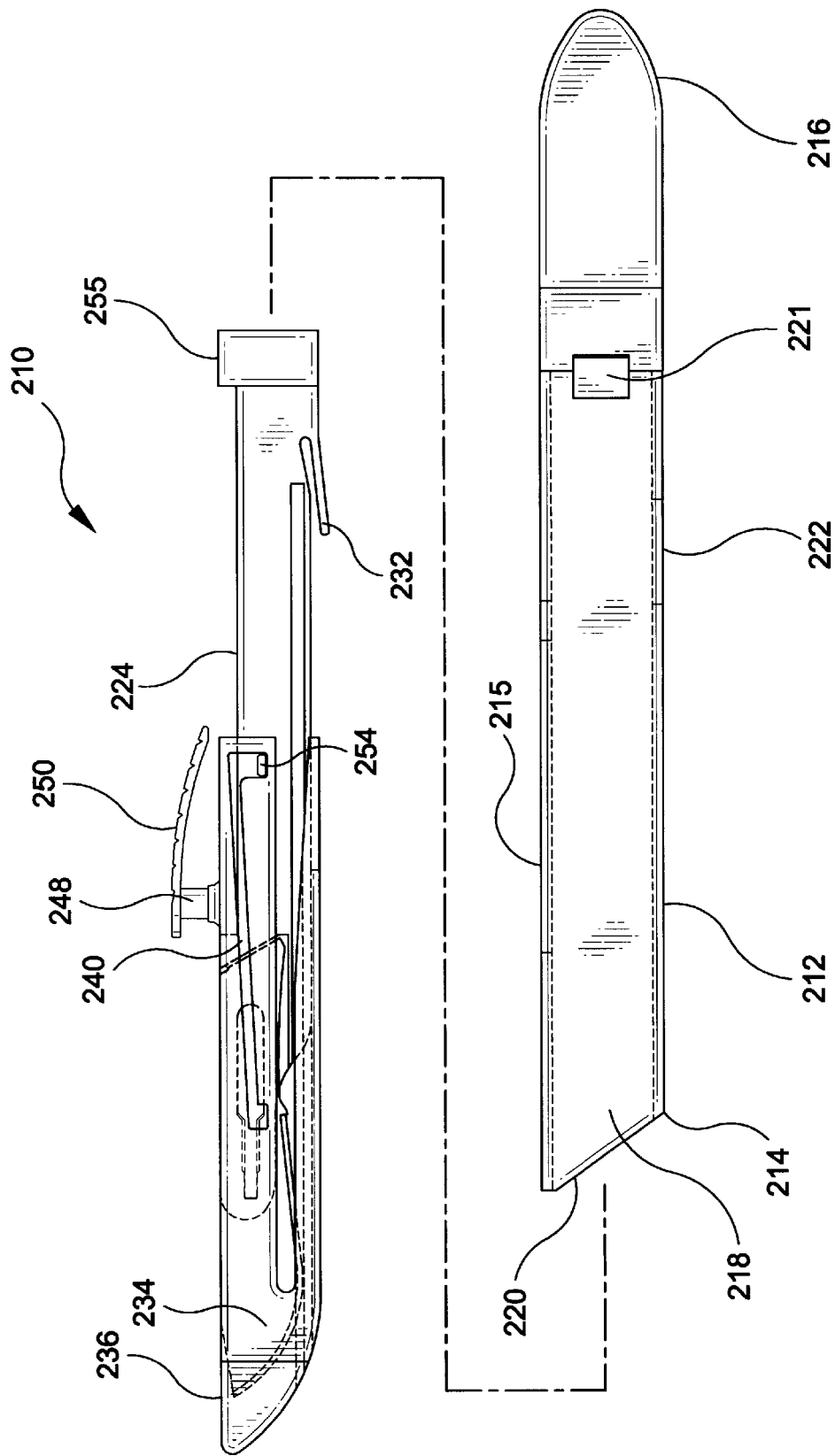
FIG. 20 is a schematic side elevation of the scalpel of the invention as shown in FIG. 17.

Another preferred embodiment of the surgical scalpel of the present invention is illustrated in FIGS. 16–32. In this embodiment, a surgical scalpel 210 includes a handle 212 that has a proximal end 216 and a distal end 214 that defines a cavity 218 with an open distal end 220 and a proximal stop 221. Within handle 212, there is an opening 222. 10 further includes a cartridge 224 that is removably mountable to handle 212. Cartridge 224 includes a blade holder 226 with a proximal end 228 and a distal end 230. Proximal end 228 of blade holder 226 includes a flexible cantilever 232 that is self-biased and positioned to engage releasably opening 222 in handle 212 when cartridge 224 is inserted into open distal end 220 of cavity 218 and moved toward proximal stop 221 in cavity 218. Flexible cantilever 232 thereby is engaged with opening 222 and retains cartridge 224 in the handle. Cartridge 224 has a blade 234 that is fixedly attached to blade holder 226 so that blade 234 projects distally when cartridge 224 is mounted to handle 212. Cartridge 224 also has a shield 236 that is mounted on blade holder 226 for slidable movement between a distal position best seen in FIGS. 17, 18 and 20 wherein shield 236 substantially prevents inadvertent access to blade 234 and a proximal position, best seen in FIGS. 19 and 23, wherein shield 236 is substantially contained within handle 212 and blade 234 is exposed for use. Shield 236 has a latch 238 for engaging blade holder 226 and releasably retaining shield 236 in the distal position and the proximal position.

Figure 21:
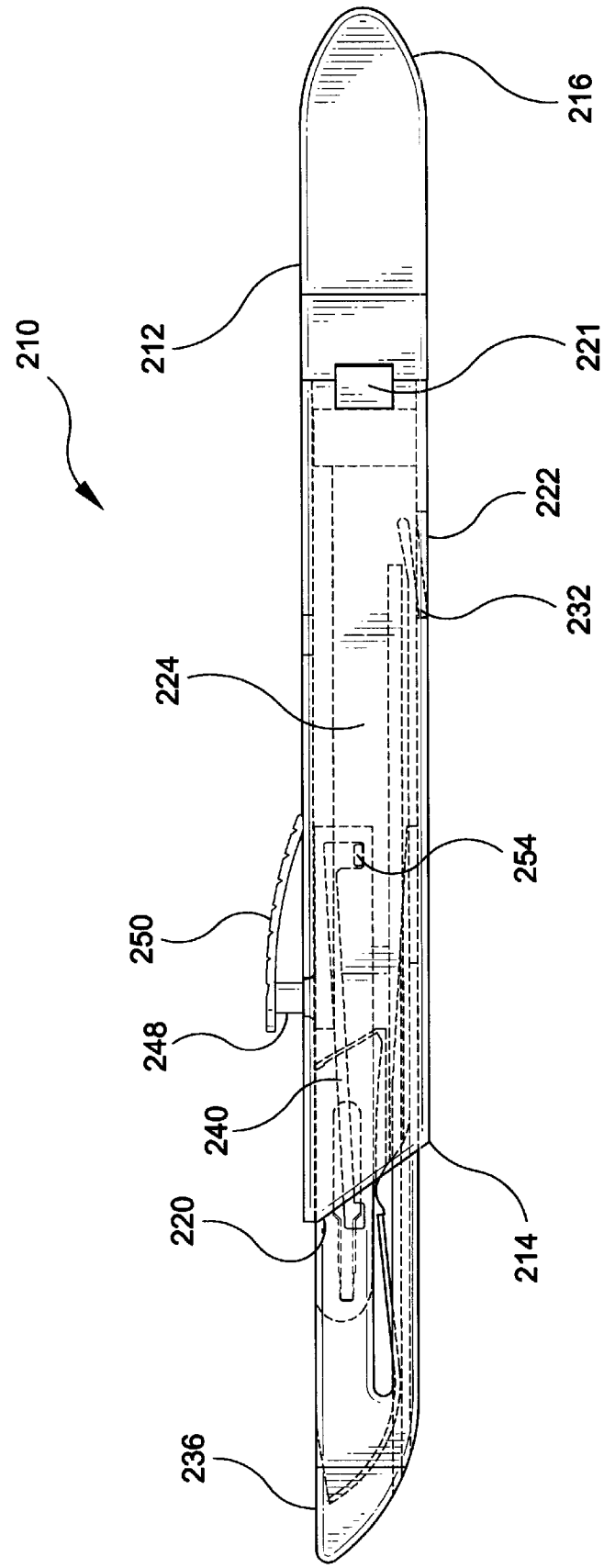
FIG. 21 is a schematic side elevation of the scalpel of the invention as shown in FIG. 18.
Figure 22:
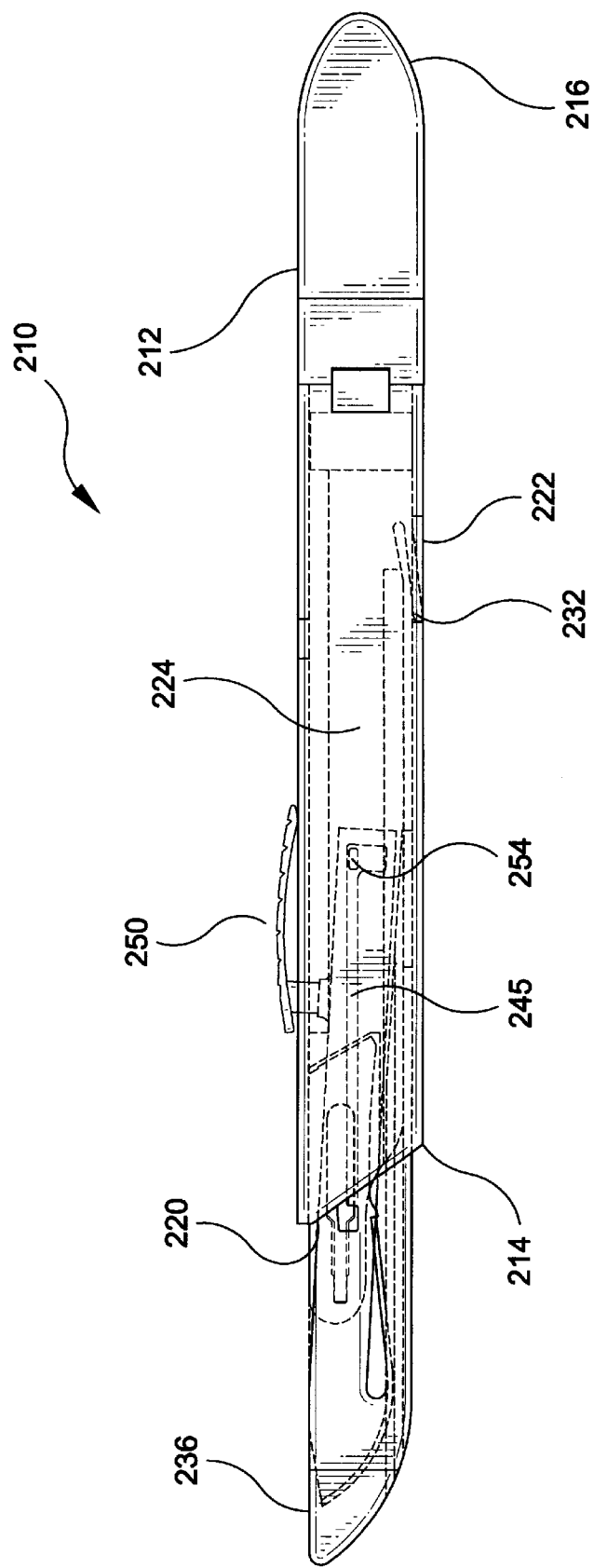
FIG. 22 is a schematic side elevational view, analogous to FIG. 21, with the digit press surface pressed in preparation to move the shield from the distal position to the proximal position.
Figure 23:
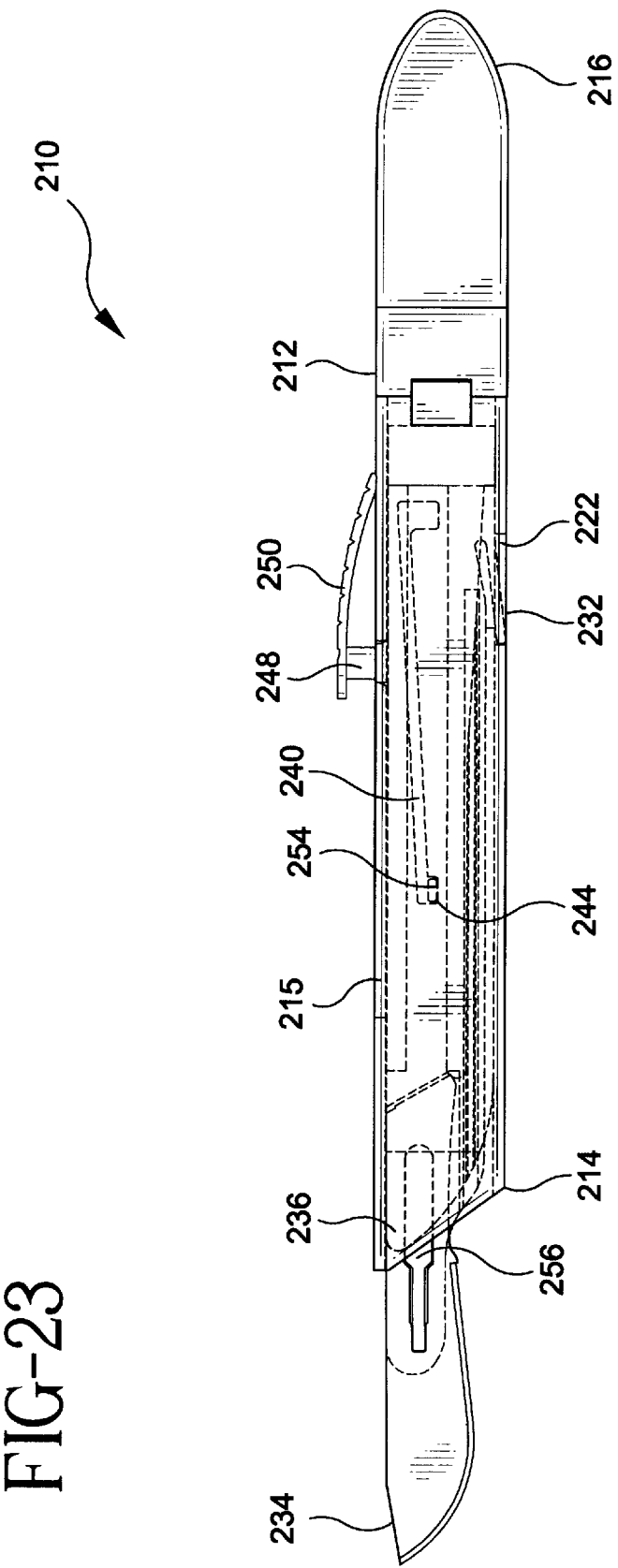
FIG. 23 is a schematic side elevational view, analogous to FIGS. 21 and 22, with the shield in the proximal position.
Figure 24:
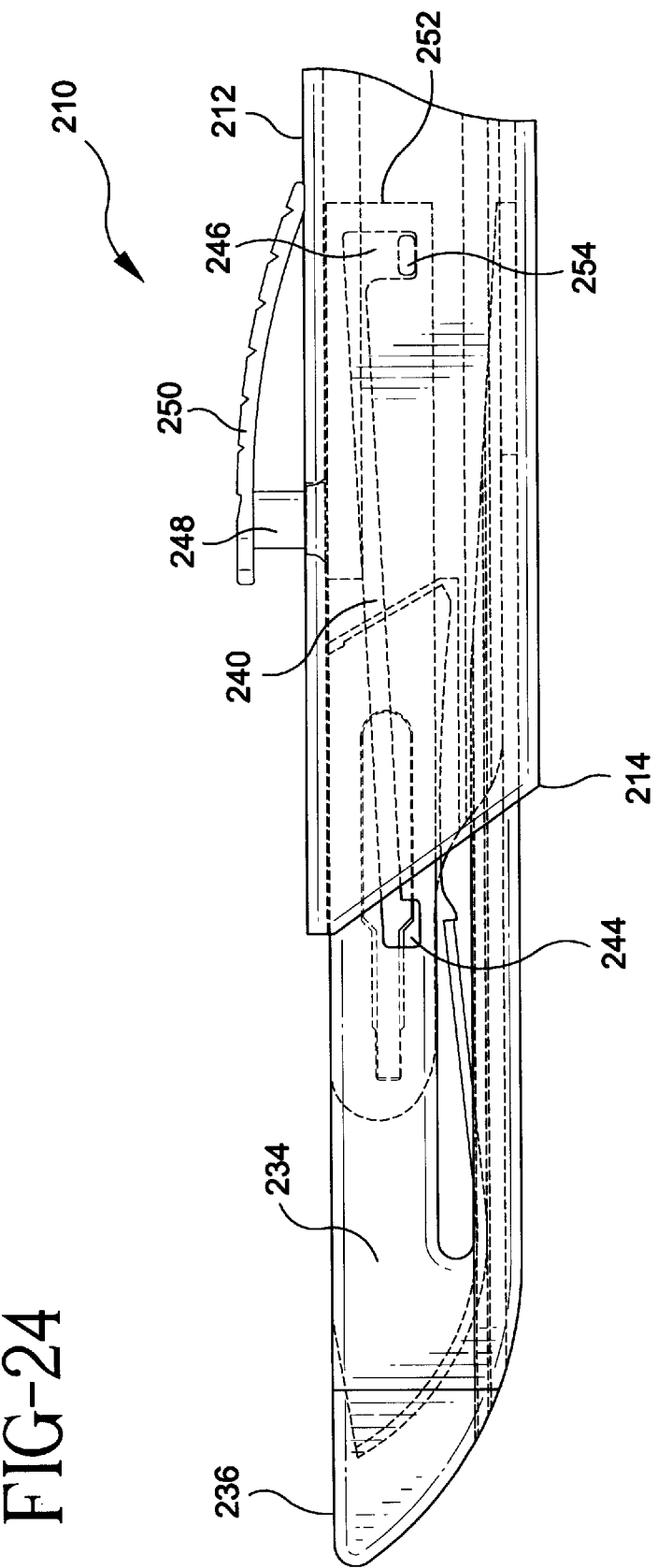
FIG. 24 is an enlarged schematic side elevational partial view of the distal portion of the scalpel from FIG. 21.
Figure 25:
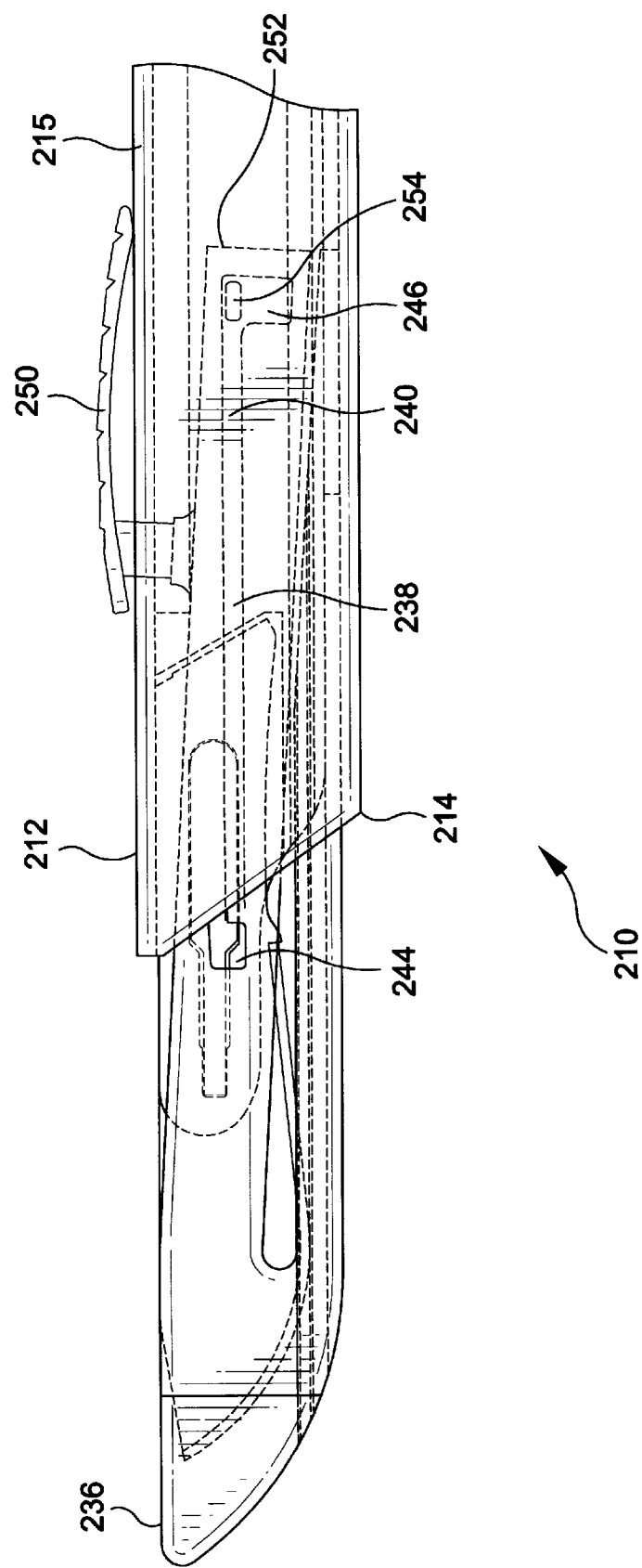
FIG. 25 is an enlarged schematic side elevational partial view of the distal portion of the scalpel from FIG. 22.
Figure 26:
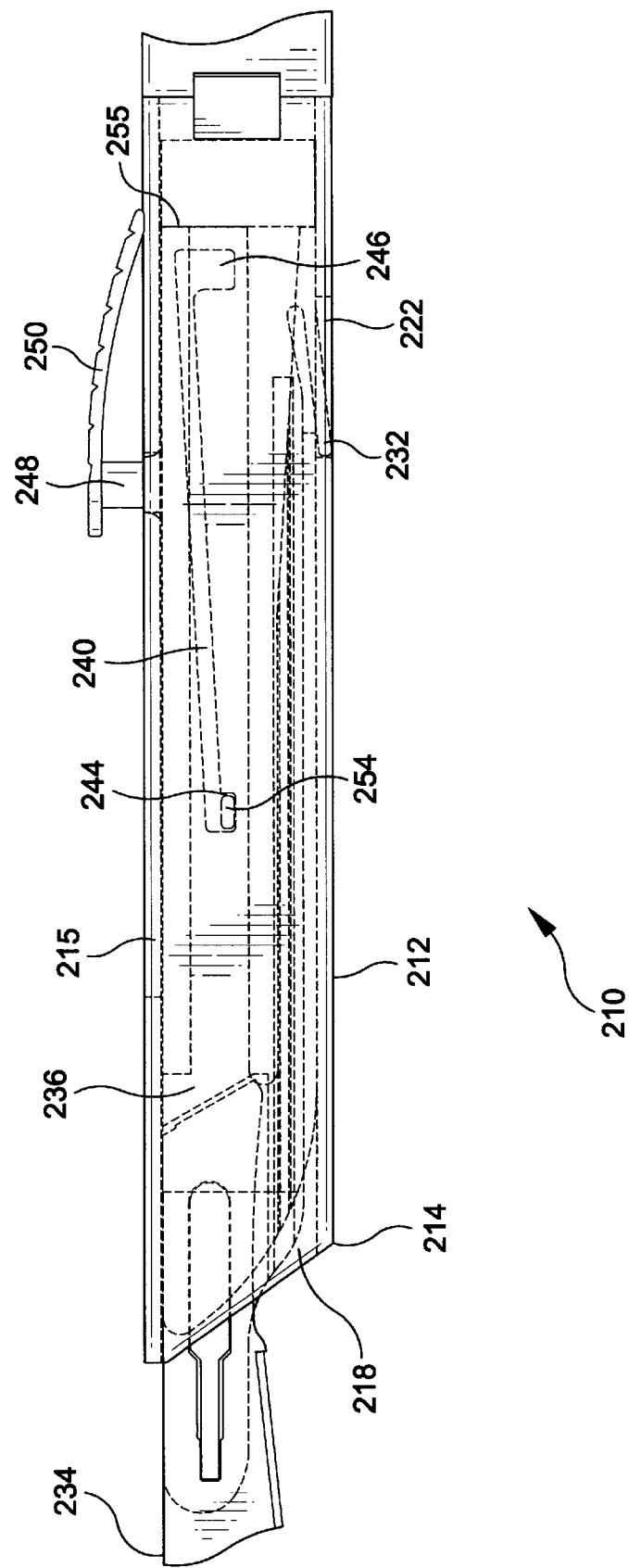
FIG. 26 is an enlarged schematic side elevational partial view of the central section of the scalpel taken from FIG. 23.

Referring to FIGS. 21, 22 and 23, cartridge 224 is removable from handle 212 only when shield 236 is in the distal position because shield 236 substantially prevents cantilever 232 from flexing inwardly from opening 222 when the shield is in the proximal position. The removal of cartridge 224 is accomplished by a practitioner overcoming the self-bias of cantilever 232 with digital pressure when the shield is in the distal position to flex cantilever 232 inwardly and to release cantilever 232 from opening 222 thereby allowing the distal withdrawal of cartridge 224 from open distal end 220 of the handle.

Referring to FIGS. 24, 25, 26, 31 and 32 latch 238 preferably includes two closed elongate slots 240 in opposing sidewalls 242 of shield 236 that each slot has a proximal stop position 244 and a distal stop position 246. Shield 236 preferably has a cantilevered tab 248 that includes a digit press surface 250 disposed at a proximal end 252 of shield 236 so that digit press surface 250 projects above handle 212 through an elongate void 215 in the handle when cartridge 224 is mounted to handle 212. Latch 238 preferably further includes two lugs 254 projecting outwardly on opposite sides of blade holder 226 that are disposed to fit within closed elongate slots 240 and engage distal stops 246 when shield 236 is in the distal position, best seen in FIG. 24, and engage proximal stops 244 when said shield is in said proximal position, best seen in FIG. 26. Lugs 254 are preferably disengaged from either of the stops by a practitioner's digital pressure on said press surface 250 sufficient to deflect proximal end 252 of shield 236 and move the stop positions away from lugs 254 on blade holder 226, best seen in FIG. 25. The practitioner's digital pressure then is able to urge movement of shield 236 from one of the positions to the other of the positions thereby allowing the practitioner selectively to expose or to prevent access to blade 234. Additionally, blade holder 226 further preferably also includes a proximal shoulder 255. Proximal shoulder 255 is positioned to engage proximal stop 221 when cartridge 224 is substantially within cavity 218. Proximal shoulder 255 also serves to limit the proximal movement of shield 236 and helps to provide additional rigidity to scalpel 210 when shield 236 is in the proximal position.

Figure 29:
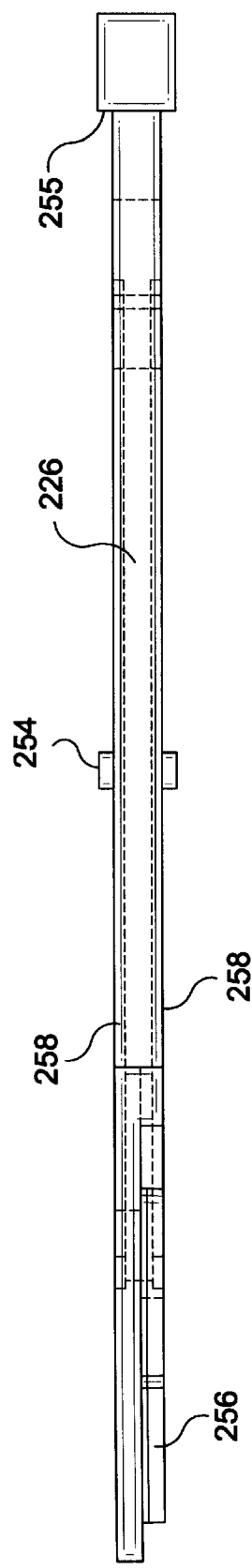
FIG. 29 is a schematic top plan view of the blade holder portion of the scalpel of FIG. 16.
Figure 30:
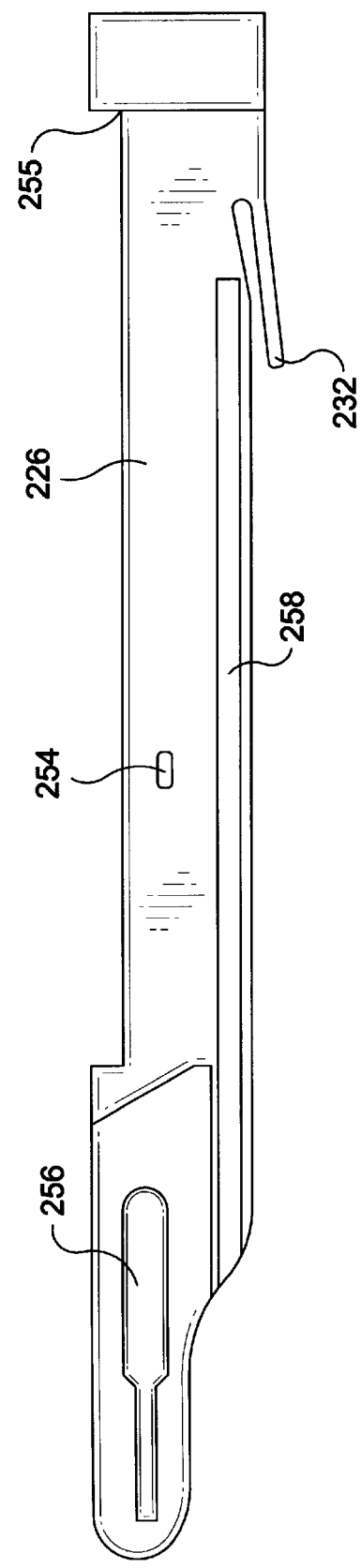
FIG. 30 is a side elevation view of the blade holder portion of the scalpel of FIG. 16.

The movement of shield 236 between the proximal and distal positions is further facilitated by at least one, preferably two channels 258 that project outwardly from opposite sides of blade holder 226, best seen in FIGS. 29 and 30, that are disposed to cooperate with at least one, preferably two guide rails 260 disposed to engage channels 258 so that as the shield is moved between the proximal and distal positions, guide rails 260 follow the channels to direct the movement of the shield between the proximal and distal positions.

Figure 16:
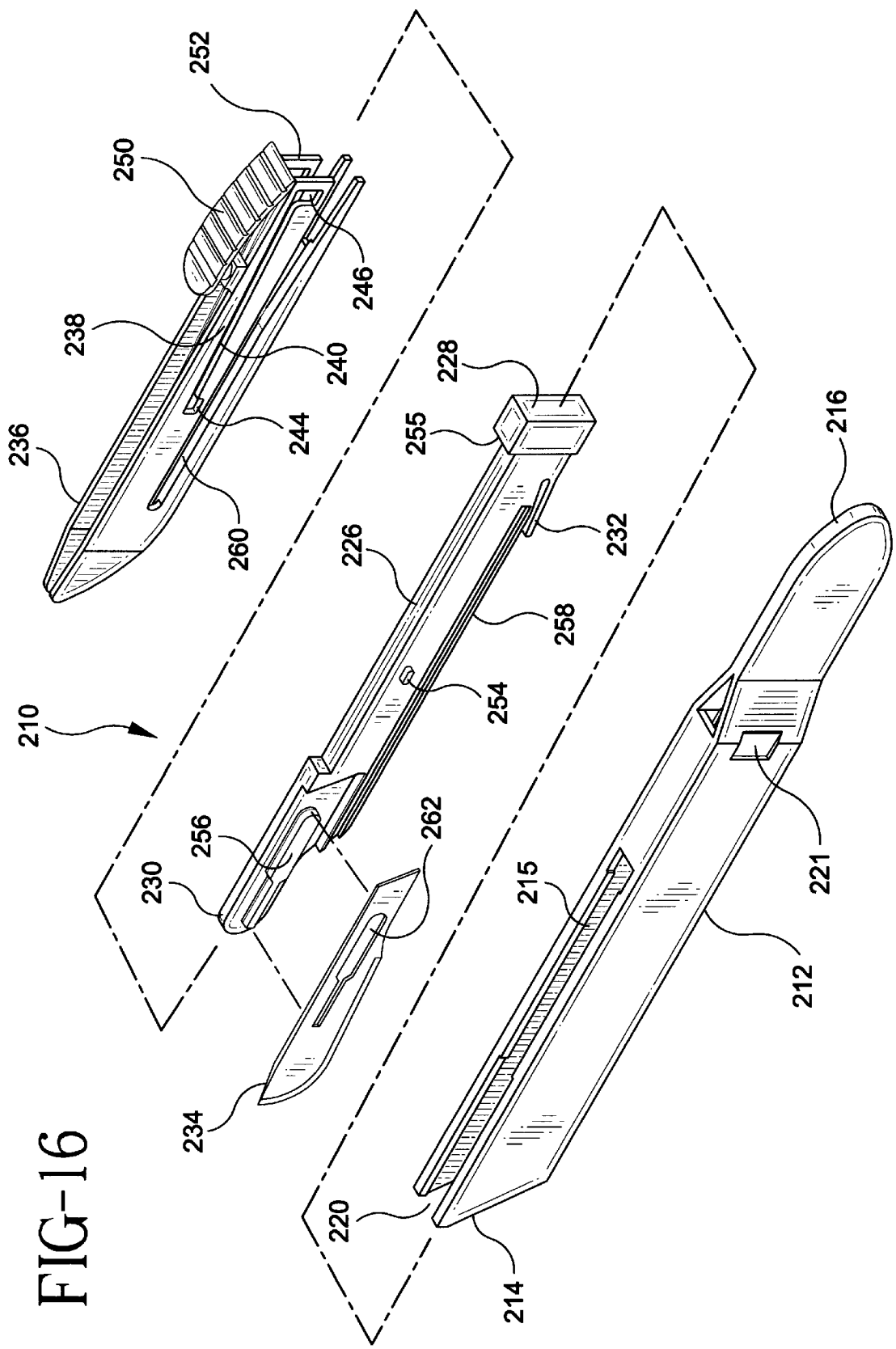
FIG. 16 is an exploded perspective view of yet another embodiment of the surgical scalpel of the invention.

Referring to FIG. 16, blade holder 226 includes an outward projection 256 sized and shaped to fit an aperture 262 in blade 234 for mounting blade 234. Blade 234 may be fixedly attached to the blade holder by heat staking, adhesive bonding or any other type of attachment known to be satisfactory for forming such an attachment. It is the intention of the invention that blade 234 not be removable from the blade holder without rendering the blade holder substantially non-functional. Preferably, blade 234 is fixedly attached to blade holder 226 by a heat staking process to provide the fixed and substantially rigid attachment of the blade that is required by practitioners. Blade 234 may be any size or shape blade commonly used for surgical procedures and formed from any materials commonly used for such blades. Preferably, blade 234 is formed from a stainless steel and sharpened to a fine cutting edge.

Blade holder 226 may be formed from thermoplastic materials such as polypropylene, polyethylene, polycarbonate, polysulfone, polyacetal, polyamide and the like. Shield 236, best seen in FIGS. 31 and 32, may be formed from thermoplastic materials such as polypropylene, polyethylene, polycarbonate, polyacetal, and polyamide and the like. For particular applications shield 236 may be formed from a substantially transparent material. Handle 212, best seen in FIGS. 27 and 28, may be formed from a material such as machined metal, formed powdered metal and thermoplastic or thermoset materials. In the preferred application, shield 236 and blade holder 226 are formed from thermoplastic materials such as polypropylene and polycarbonate with a stainless steel blade to form the single-use cartridge 224. Handle 212 preferably is formed from machined metal or formed powdered metal to provide a durable reusable device that provides the practitioners with the same "feel" and "heft" that they are accustomed to with the current reusable handles and with removable single-use bare blades.

Figure 17:
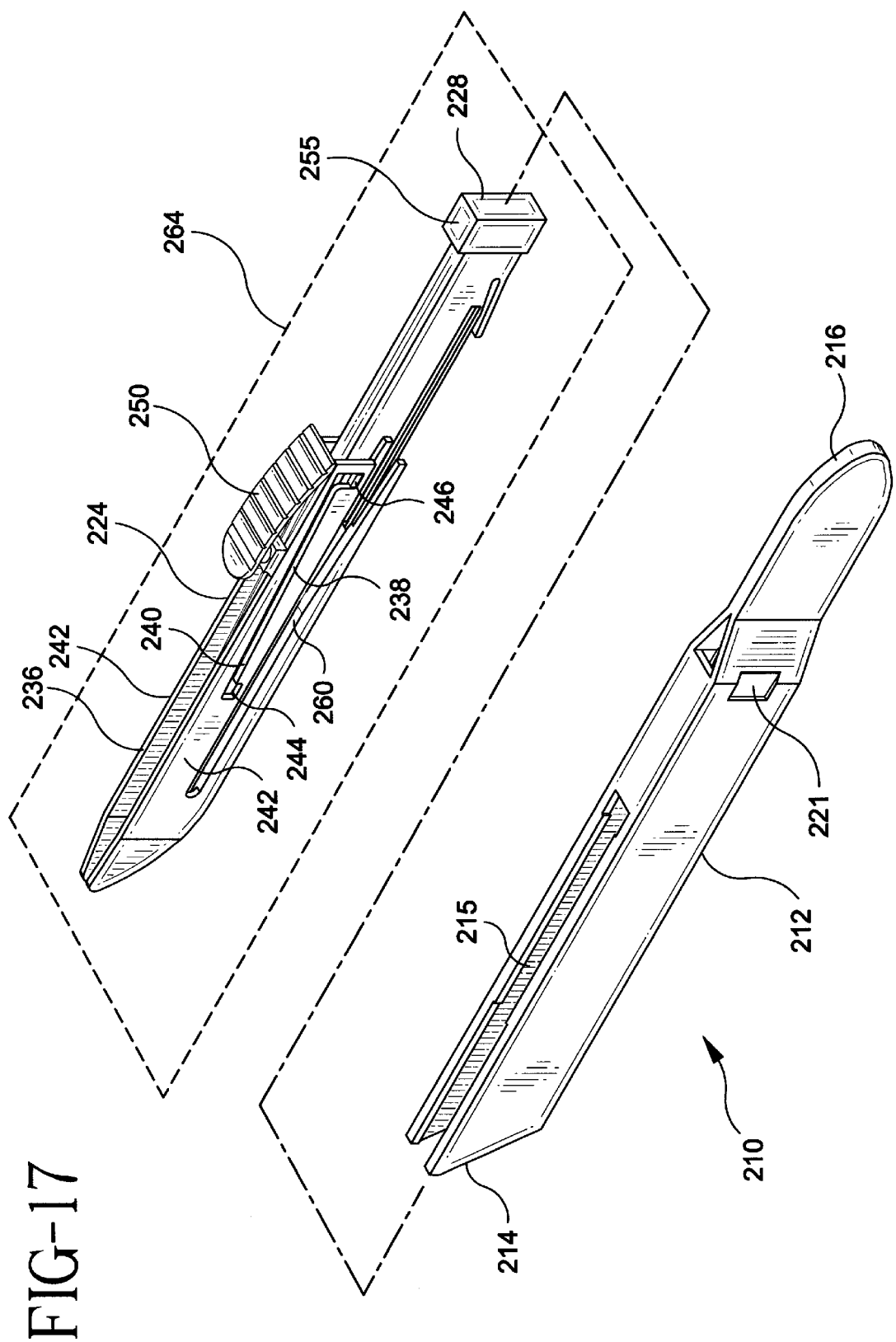
FIG. 17 is a partially exploded perspective view of the surgical scalpel of FIG. 16.

Preferably, cartridge 224, with shield 236 in the distal position where blade 234 is protected, is placed in a package 264, indicated in phantom in FIG. 17, formed from materials substantially resistant to the passage of microorganisms and package 264 is sealed. Preferably, sealed package 264 is then exposed to conditions that would render any microorganisms inside the package substantially non-viable. Packaged cartridges then may be considered "sterile" until the package is opened to arm the reusable handle. Preferably, the handles are subjected to a cleaning and sterilization process by the practitioner prior to their presentation for the cartridge loading. Suitable materials for forming package 264 include, but are not limited to, paper, nonwoven materials such as spun-bonded polyolefin and the like, polymeric films, metallic foils and composites of these materials. Suitable techniques for rendering microorganisms within package 264 non-viable include, but are not limited to, exposure to chemical agents such as ethylene oxide, gaseous hydrogen peroxide and the like, ionizing radiation, such as gamma radiation from $Co^{60}$, electron beam radiation, dry heat and steam sterilization. When selecting materials for forming scalpel 210 and package 264, consideration of the particular materials' tolerance for the sterilization method should be made.

A method for using scalpel 210 includes opening package 264 to expose proximal end 228 of cartridge 224. Handle 212 is then fitted to the cartridge and removed from the package. Depending upon the choice of the individual practitioner or the institution use protocol, scalpel 210 may be passed to the practitioner with shield 236 in the distal position as it is removed from package 264. Upon receiving scalpel 210, the practitioner applies digital pressure to press surface 250 to disengage lugs 254 from distal stops 246 and withdraw shield 236 to the proximal position to expose blade 234 for the desired procedure. After the practitioner has completed the procedure, the practitioner applies digital pressure to press surface 250 to disengage lugs 254 from proximal stops 244 and return shield to the distal position to pass scalpel 210 to the support person with blade 234 protected from inadvertent exposure. With shield 236 in the distal position, the support personnel may then remove cartridge 224 from handle 212 and dispose of it according to the institution protocol. Handle 212 may then be subject to cleaning and sterilization according to the institution protocol and returned for further use.

An alternative for particular applications, is to form handle 212 from similar materials as blade holder 226, mount cartridge 224 to handle 212, complete the desired procedure, and then dispose of entire scalpel 210 after the procedure is completed. Another alternative, useful for some applications, is to integrally form handle 212 and blade holder 226. When handle 212 and blade holder 226 are integrally formed, the entire scalpel is intended to be used only once and disposed of.

The invention provides practitioners and support personnel with an intuitive-to-use scalpel that substantially protects personnel from inadvertent exposure to scalpel blades and still provides the practitioner with a tool that has substantially the same "feel" as the currently used scalpels. Cartridge 224 may be made available with blade 234 available in any current size and shape desired for particular applications. Scalpel 210 substantially reduces the possibility of an inadvertent exposure of the blade to the practitioner or support personnel.

What is claimed is:

1. A surgical scalpel comprising:
    a handle having a proximal end and a distal end that defines a cavity with an open distal end within said handle, said handle further including an opening;
    a cartridge removably mounted to said handle, said cartridge including a blade holder with a proximal end and a distal end, said cartridge having means for removably mounting said cartridge to said handle;
    a blade fixedly attached to said blade holder so that said blade projects distally when said cartridge is mounted to said handle; and
    a shield mounted on said blade holder for slidable movement between a distal position wherein said shield substantially prevents inadvertent access to said blade and a proximal position wherein said shield is substantially contained within said handle and said blade is exposed for use, said shield having latch means for engaging said blade holder and releasably retaining said shield in said distal position and said proximal position.

2. The surgical scalpel of claim 1 wherein said means for removably mounting said cartridge to said handle comprises a flexible cantilever on said blade holder self-biased and positioned to engage releasably said opening in said handle when said cartridge is inserted into said open distal end of said cavity and moved toward said proximal end, said flexible cantilever thereby engaging said opening and retaining said cartridge in said handle.

3. The surgical scalpel of claim 2 wherein said cartridge is removable from said handle only when said shield is in said distal position by said shield substantially preventing said cantilever from flexing from said opening when said shield is in said proximal position, said removal being accomplished by overcoming said bias of said cantilever when said shield is in said distal position to release said cantilever from said opening thereby allowing withdrawal of said cartridge from said open distal end of said handle.

4. The surgical scalpel of claim 1 wherein shield further comprises a first sidewall and a second sidewall and wherein said latch means for engaging said blade holder and releasably retaining said shield in said proximal position and said distal position comprises at least one closed elongate slot in one of said sidewalls of said shield, said at least one closed elongate slot having a proximal stop position and a distal stop position, said shield having cantilevered tab including a digit press surface disposed at a proximal end of said shield so that said digit press surface projects above said handle when said cartridge is mounted to said handle, said latch means further comprising at least one lug on said blade holder sized and positioned to fit within said at least one closed elongate slot and to engage said distal stop when said shield is said distal position and engage said proximal stop when said shield is in said proximal position, said lug being disengaged from said either of said stops by a practitioner's digital pressure on said digit press surface sufficient to deflect said proximal end of said shield and to move said stop position away from said lug on said blade holder, said pressure then to urge movement of said shield from one of said positions to the other of said positions thereby allowing the practitioner selectively to expose or to prevent access to said blade.

5. The surgical scalpel of claim 4 wherein said latch means comprises two elongate closed slots, one slot in each of said sidewalls of said shield, and two lugs positioned and sized to fit within each of said slots.

6. The surgical scalpel of claim 1 wherein said blade holder further comprises an outward projection and said blade further comprises an aperture therethrough sized to engage said outward projection, said blade being fixedly attached to said blade holder by positioning said aperture in said blade over said projection.

7. The surgical scalpel of claim 6 wherein said blade is fixedly attached to said outward projection of said blade holder by bonding technique selected from the group consisting of heat staking and adhesive bonding.

8. The surgical scalpel of claim 1 wherein said blade holder further comprises a proximal shoulder to limit the proximal movement of said shield.

9. The surgical scalpel of claim 1 wherein said blade holder further includes at least one channel projecting outwardly and said shield further includes at least one guide rail disposed to engage said channel so that as said shield is moved between said proximal and said distal positions, said guide rail follows said channel to direct said movement of said shield between said proximal and distal positions.

10. The surgical scalpel of claim 9 wherein said blade holder comprises two opposing sides, each side having a channel projecting outwardly therefrom and said shield comprises two guide rails disposed to engage said two channels.

11. The surgical scalpel of claim 1 wherein said blade holder is formed from a thermoplastic material selected from the group consisting of polypropylene, polyethylene, polycarbonate, polysulfone, polyacetal and polyamide.

12. The surgical scalpel of claim 1 wherein said shield is formed from a thermoplastic material selected from the group consisting of polypropylene, polyethylene, and polycarbonate, polyacetal, and polyamide.

13. The surgical scalpel of claim 12 wherein said shield is formed from a substantially transparent material.

14. The surgical scalpel of claim 1 wherein said handle is formed from a material selected from the group consisting of machined metal, formed powdered metal and thermoplastic materials.

15. The surgical scalpel of claim 1 further comprising said cartridge being placed in a package formed from materials substantially resistant to the passage of microorganisms and exposed to conditions that render any microorganisms therein substantially nonviable.

16. A cartridge removably mountable on a handle to form a surgical scalpel comprising:
 a blade holder with a proximal end and a distal end, said blade holder having means for removably mounting said cartridge to the handle;
 a blade fixedly attached to said blade holder so that said blade projects distally when said cartridge is mounted to the handle; and
 a shield mounted on said blade holder for slidable movement between a distal position wherein said shield substantially prevents inadvertent access to said blade and a proximal position wherein said shield is substantially contained within the handle and said blade is exposed for use, said shield having latch means for engaging said blade holder and releasably retaining said shield in said distal position and said proximal position.

17. The cartridge of claim 16 further comprising said cartridge being placed in a package formed from materials substantially resistant to the passage of microorganisms and exposed to conditions that render any microorganisms therein substantially nonviable.

18. A surgical scalpel comprising:
 a handle having a proximal end and a distal end that defines a cavity with an open distal end within said handle, said handle further including an opening;
 a cartridge removably mountable to said handle, said cartridge including a blade holder with a proximal end and a distal end, said blade holder having a flexible cantilever biased and positioned to engage releasably an opening in said handle when said cartridge is inserted into said open distal end of said cavity and moved toward said proximal end, said flexible cantilever thereby engaging said opening and retaining said cartridge in said handle;
 a blade fixedly attached to said blade holder so that said blade projects distally from said blade holder; and
 a shield mounted on said blade holder for slidable movement between a distal position wherein said shield substantially prevents inadvertent access to said blade and a proximal position wherein said blade is exposed for use and said shield is substantially contained within said handle, said shield having latch means for engaging said blade holder and releasably retaining said shield in said distal position and said proximal position, said shield substantially preventing removal of said cartridge from said handle when said shield is in said proximal position by substantially preventing flexation of said cantilever to disengage said cantilever from said opening.

19. A method for preparing a surgical scalpel for use comprises:
 providing a handle for a scalpel;
 providing a sealed package containing a cartridge removably mountable on said handle comprising a blade holder with a proximal end and a distal end, said blade holder having means for removably mounting said cartridge to the handle, a blade fixedly attached to said blade holder so that said blade projects distally when said cartridge is mounted to the handle and a shield mounted on said blade holder for slidable movement between a distal position wherein said shield substantially prevents inadvertent access to said blade and a proximal position wherein said shield is substantially contained within the handle and said blade is exposed for use, said shield having latch means for engaging said blade holder and releasably retaining said shield in said distal position and said proximal position;
 opening said package said proximal end of said cartridge;
 fitting said handle to said proximal end of said cartridge to form the scalpel;
 removing said cartridge from said package; and
 moving said shield from said proximal position to said distal position, thereby exposing said blade for use.

* * * * *